United States Patent
Wang et al.

(10) Patent No.: US 10,253,024 B2
(45) Date of Patent: Apr. 9, 2019

(54) POLYCYCLIC INDOLINE AND INDOLENINE COMPOUNDS

(71) Applicant: The Regents of the University of Colorado, a body corporate, Denver, CO (US)

(72) Inventors: Xiang Wang, Superior, CO (US); Patrick Barbour, Boulder, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 0 days.

(21) Appl. No.: 15/569,186

(22) PCT Filed: Apr. 29, 2016

(86) PCT No.: PCT/US2016/030233
§ 371 (c)(1),
(2) Date: Oct. 25, 2017

(87) PCT Pub. No.: WO2016/176634
PCT Pub. Date: Nov. 3, 2016

(65) Prior Publication Data
US 2018/0148442 A1 May 31, 2018

Related U.S. Application Data

(60) Provisional application No. 62/154,792, filed on Apr. 30, 2015.

(51) Int. Cl.
| | |
|---|---|
| *C07D 471/04* | (2006.01) |
| *C07D 471/10* | (2006.01) |
| *C07D 471/18* | (2006.01) |
| *A61P 31/04* | (2006.01) |
| *A61K 31/437* | (2006.01) |
| *A61K 45/06* | (2006.01) |

(52) U.S. Cl.
CPC .......... *C07D 471/04* (2013.01); *A61K 31/437* (2013.01); *A61K 45/06* (2013.01); *A61P 31/04* (2018.01); *C07D 471/10* (2013.01); *C07D 471/18* (2013.01)

(58) Field of Classification Search
CPC .. C07D 471/04; C07D 471/10; C07D 471/18; A61P 31/04; A61K 31/437; A61K 45/06
USPC ......................................................... 514/210
See application file for complete search history.

(56) References Cited

U.S. PATENT DOCUMENTS

2013/0210803 A1  8/2013  Chakravarty et al.
2014/0364609 A1  12/2014  Tomesch et al.

FOREIGN PATENT DOCUMENTS

WO    WO 2014/165548 A2    10/2014

OTHER PUBLICATIONS

Patani et al. Bioisosterism; A rational approach in drug design. (Year: 1996).*
Barbour, Patrick et al., "Property-Guided Synthesis of Aza-Tricyclic Indolines: Development of Gold Catalysis En Route," Advanced Synthesis & Catalysis. Mar. 3, 2016, vol. 358, p. 1482-1490.
International Search Report of PCT/US16/30233, dated Aug. 5, 2016.
International Preliminary Report on Patentability of PCT/US16/30233, dated Oct. 31, 2017.

* cited by examiner

*Primary Examiner* — Rita J Desai
(74) *Attorney, Agent, or Firm* — Don D. Cha; Hamilton DeSanctis & Cha, LLP

(57) ABSTRACT

The present invention relates to indoline and indolenine alkaloid compounds. In particular, indoline and indolenine alkaloid compounds of the invention have antibacterial activity and/or are capable of re-sensitizing the susceptibility of methicillin-resistant *S. aureus* to a β-lactam antibiotic. The present invention also relates to a method for producing and using the same.

17 Claims, No Drawings

POLYCYCLIC INDOLINE AND INDOLENINE COMPOUNDS

CROSS-REFERENCE TO RELATED APPLICATIONS

This application claims the priority benefit of U.S. Provisional Application No. 62/154,792, filed Apr. 30, 2015, which is incorporated herein by reference in its entirety.

FIELD OF THE INVENTION

The present invention relates to nitrogen-containing polycyclic indoline and indolenine compounds. In particular, compounds of the invention have antibacterial activity and/or are capable of re-sensitizing methicillin-resistant *S. aureus* to β-lactam antibiotic. The present invention also relates to a method for producing and using the same.

BACKGROUND OF THE INVENTION

Emergence of conventional antibiotic resistant bacteria has become a major worldwide health threat. Currently, development of new antibiotics has lagged far behind. Antibiotics are one of the most important and widely used medicines. Unfortunately, their extensive use has led to the development of resistance by their pathogenic bacterial targets. The emergence of multi-drug resistant bacteria has become a global public health threat. Serious infection from multi-drug resistant microorganisms often causes considerable patient mortality and modality.

It has been reported that more people died from methicillin-resistant *Staphylococci aureus* (MRSA) infection than those from HIV/AIDS, Parkinson's disease and homicide combined. *S. aureus* is the most common Gram-positive bacteria pathogen that can cause skin infection, respiratory disease, and food poisoning. It is believed that there are two predominant resistance mechanisms in MRSA. One of the resistance mechanisms is believed to be the presence of mecA gene that encodes penicillin-binding protein 2a (PBP2a). PBP2a has been shown to have a low affinity to β-lactam antibiotics such as methicillin, thereby allowing sufficient peptidoglycan cross-linking in the presence of β-lactam antibiotics. The second resistance mechanism is the presence of blaZ gene. BlaZ gene encodes β-lactamases that chemically deactivate β-lactam antibiotics.

The pharmaceutical industry has been developing structural analogs of β-lactam antibiotics that have higher affinity to PBP2a and lower activity to β-lactamases. This strategy has kept up with the emergence of new resistant MRSA strains until recently. However, there are not enough analogs in development to combat current and future resistance emergence.

Recently, use of resistance-modifying agents (RMAs) in combination with antibiotics has been used to extend the usefulness of conventionally available antibiotics. Without being bound by any theory, it is believed that RMAs target non-essential resistance conferring genes thereby further expanding the life span of antibiotics that are currently used in the clinics. RMAs are particularly useful because currently used antibiotics have already been optimized for toxicity and large-scale production. For example, clavulanic acid is a serine-dependent β-lactamase inhibitor from *Streptomyces clavuligerus*. Its use in combination with amoxicillin restores the efficacy of amoxicillin against bacteria producing β-lactamases, and this combination has become one of the most prescribed antibiotics in the United States.

With the discovery of clavulanic acid, numerous efforts have attempted to discover other RMAs from natural sources, such as membrane permeablizing agents and inhibitors of efflux pumps. Currently, the only RMAs that have been proven clinically useful are β-lactamase inhibitors.

There have been a number of reports recently that showed plant extracts from a variety of different species can potentiate the activity of β-lactam antibiotics. However, the discovery of the active compounds has been very difficult. This challenge is due to the chemical complexity of plant extracts, the lack of standardization, difficulties in access and supply, and the inherent slowness and costs of working with natural products. Only a few plant natural products with RMA activity have been characterized, such as epigallocatechin gallate (i.e., EGCG, a flavonoid from green tea) and reserpine (i.e., a polycyclic indole alkaloid from the root of an Indian medical plant.

Therefore, there is a continuing and urgent need for RMAs that can extend the usefulness of antibiotics for the treatment of drug resistant bacteria.

SUMMARY OF THE INVENTION

Some aspects of the invention provide a resistance-modifying agent ("RMA"). Without being bound by any theory, it is believed that RMAs target non-essential, resistance-conferring genes and restore antibiotic sensitivity of a bacteria. A notable advantage of RMAs is that they are capable of extending the market lifespan of known antibiotics that have already been optimized for large-scale production with well-studied toxicity profiles. One particular aspect of the invention provides an azaindoline alkaloid compound ("azaindoline compound") that selectively re-sensitizes methicillin-resistant *S. aureus* to β-lactam antibiotics, such as oxacillin, amoxicillin/clavulanic acid, meropenem and cefazolin. Azaindoline compounds of the invention can be used in combination with β-lactam antibiotics to treat antibiotic resistant bacterial infections. Moreover, some of the azaindoline compounds of the invention are effective antibiotics in and of themselves.

In one particular embodiment, the compound of the invention is of the formula:

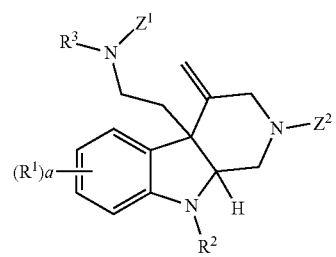

A where a is 1 or 2; each $R^1$ is independently halide; each of $R^2$, $R^3$ and $Z^1$ is independently hydrogen, alkyl or a nitrogen protecting group; and $Z^2$ is hydrogen, alkyl, a nitrogen protecting group or a moiety of the formula —C(=O)—$R^4$, wherein $R^4$ is biotin, alkyl, haloalkyl, alkylene(alkynyl), $NR^5Ar^1$ (wherein $R^5$ is hydrogen or alkyl and $Ar^1$ is optionally substituted aryl), provided at most only one of $Z^1$ and $R^3$ is a nitrogen protecting group.

In some embodiments, a in Compound of Formula A is 2. Still in other embodiments, each of $R^1$ in Compound of Formula A is independently selected from the group consisting of hydrogen, Cl, Br, and F. Yet in one particular embodiment, the compound of the invention is of the formula:

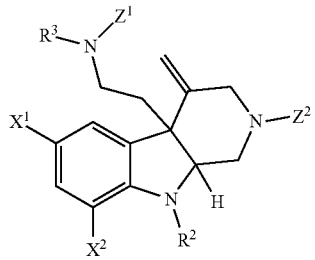

A-1 where $R^2$, $R^3$, $Z^1$ and $Z^2$ are those defined herein, and each of $X^1$ and $X^2$ is independently selected from the group consisting of hydrogen, Cl, Br and F, provided at least one of $X^1$ and $X^2$ is not hydrogen. In some instances, $X^2$ in Compound of Formula AI is F.

Another aspect of the invention provides an antibiotic composition comprising compound described herein. In some embodiments, the antibiotic composition further comprises a β-lactam antibiotic. Exemplary β-lactam antibiotics include amoxicillin, clavulanic acid, cefazolin, meropenem, as well as other conventional β-lactam antibiotics that are known to one skilled in the art. Still in other embodiments, the antibiotic composition can also include a β-lactamase inhibitor or other resistance-modifying agent or a combination thereof.

Yet another aspect of the invention provides a method for treating bacterial infection in a subject comprising administering to the subject in need of such a treatment a therapeutically effective amount of a β-lactam antibiotic and a compound described herein.

Still another aspect of the invention provides a method for producing the azaindole compound described herein. Such a method can include producing an intermediate Compound II and converting the intermediate Compound II to an azaindole compound of the invention.

In one particular aspect of the invention, a method is provided for producing a fused-azaindoline compound of the formula:

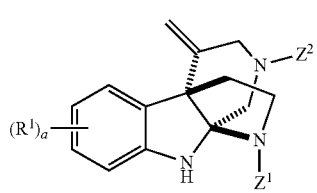

II by contacting a substituted indole compound of the formula:

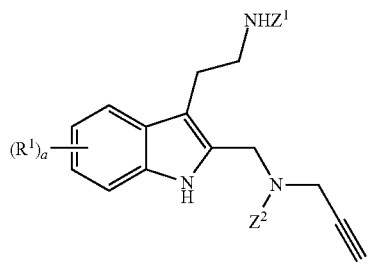

III with a gold catalyst under conditions sufficient to produce the fused-azaindoline compound of Formula II, where a is 1 or 2; each of $R^1$ is independently halide; and each of $Z^1$ and $Z^2$ is independently hydrogen, alkyl or a nitrogen protecting group. In some embodiments, the gold catalyst is Au(I)-containing organometallic complex. In one specific embodiment, the gold catalyst is $Ph_3PAuNTf_2$.

Another aspect of the invention provides a method for treating MRSA infection in a subject comprising administering to the subject having a MRSA infection a therapeutically effective amount of a β-lactam and an azaindole compound described herein. In some embodiments, the β-lactam comprises amoxicillin, clavulanic acid, cefazolin, meropenem, or a combination thereof.

It should be appreciated that Compound of Formula II can be converted into Compound of Formula A or A-1 by reduction of a carbon having two nitrogen atoms attached.

Another aspect of the invention provides a compound of the formula:

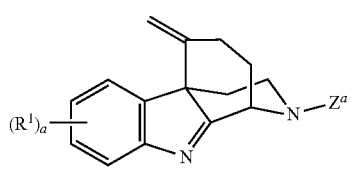

B where a is 0, 1 or 2; each $R^1$ is independently halide, alkyl or alkoxide; and $Z^2$ is hydrogen or a nitrogen protecting group. In some embodiments, a is 0 or 1. Within these embodiments, in some instances a is 1. Yet in other embodiments, $R^1$ is hydrogen or alkoxy. Some of the exemplary alkoxy groups suitable for $R^1$ include, but are not limited to, methoxy, t-butoxy, ethoxy, propoxy, iso-butoxy, iso-propoxy, and the like. Still in other embodiments, $Z^2$ is selected from the group consisting of hydrogen, —$COAr^1$, Ns, $SO_2Ar^1$, Ts, Cbz and $COCF_3$, wherein $Ar^1$ is optionally substituted phenyl. In some instances, $Ar^1$ is halo-substituted phenyl. Exemplary optionally substituted phenyls that are suitable for $Ar^1$ include, but are not limited to, phenyl, p-chlorophenyl, p-fluorophenyl and the like.

Compound of Formula B can be produced by contacting a compound of the formula:

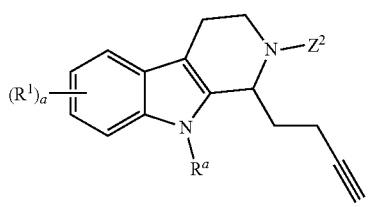

IB with a gold catalyst under conditions sufficient to produce a Compound of Formula B, where a, $R^1$ and $Z^2$ are those defined for Compound of Formula B. and $R^a$ is a nitrogen protection group. In some instances, the nitrogen protecting group $R^a$ is trialkylsilyl. Exemplary trialkylsilyl groups that are suitable for $R^a$ include, but are not limited to, trimethylsilyl, t-butyl-dimethylsilyl, triisopropylsilyl, and the like as well as other silyl groups where two or more alkyl groups attached to silicon atom may optionally form a cyclic alkyl group.

While some of the specific substituents for Compounds of the invention are disclosed herein, it should be noted that combinations of various groups described herein form other embodiments. In this manner, a variety of compounds are embodied within the present invention.

DETAILED DESCRIPTION OF THE INVENTION

Some aspects of the invention provide an azaindoline alkaloid compound (i.e., azaindoline or simply "indoline" compound) that is capable of re-sensitizing the susceptibility of methicillin-resistant *S. aureus* to a β-lactam antibiotic. In one particular embodiment, the azaindoline compound is of the formula:

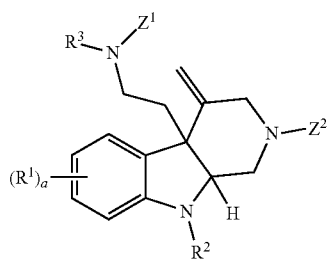

A where a is 0, 1 or 2; each $R^1$ is independently halide; each of $R^2$, $R^3$ and $Z^1$ is independently hydrogen, alkyl or a nitrogen protecting group, provided at most only one of $Z^1$ or $R^3$ is a nitrogen protecting group; and $Z^2$ is hydrogen, alkyl, a nitrogen protecting group or a carbonyl group. In some embodiments, a is 1 or 2. In other embodiments, le is independently selected from the group consisting of hydrogen, Cl, Br, and F.

In one particular embodiment, compound of Formula A is more specifically of the formula:

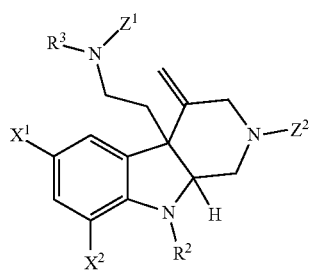

A-1 where $R^2$, $R^3$, $Z^1$ and $Z^2$ are those defined herein; and each of $X^1$ and $X^2$ is independently selected from the group consisting of hydrogen, Cl, Br and F, provided at least one of $X^1$ and $X^2$ is not hydrogen. In some instances, $X^2$ is F. Still in other instances, $X^1$ is Cl.

Referring again to compound of Formula A, in some embodiments $Z^2$ is selected from a moiety of the group consisting of: $-C(=O)R^a$, $-C(=O)[CH_2]_2CCH$, $-C(=O)CH_2NH$-tBoc, $-C(=O)CH_2NH_2$, $-C(=O)[CH_2]_5NHC(=O)[CH_2]_2-Y^1$, $-C(=O)[CH_2]_3Y^2$, $-C(=O)[CH_2]_2CO_2H$, $-C(=O)CF_3$, $-C(=O)Y^3$, -tBoc, $-SO_2-Ar^1$, $-C(=O)NHY^4$, and a guanidine derivative of the formula $-C(=NR^x)-NR^yR^z$ where each of $R^x$, $R^y$ and $R^z$ is independently H, alkyl, cycloalkyl, heterocycloalkyl, (heterocycloalkyl)alkyl, (cycloalkyl)alkyl, and heteroalkyl, $R^a$ is alkyl or haloalkyl, $Ar^1$ is aryl or heteroaryl, $Y^1$ is a moiety of the formula

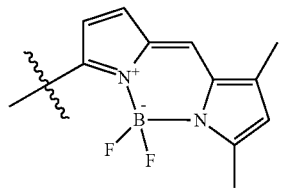

(i.e., (5,5-difluoro-7,9-dimethyl-5H-$4\lambda^4$, $5\lambda^4$-dipyrrolo[1,2-c:2',1'-f][1,3,2]diazaborinin-3-yl)), $Y^2$ is a moiety of the formula

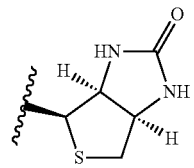 [SMILES: *[C@@H]1SC[C@@H]2NC(=O)N[C@@H]21]

(i.e., ((3aS,4S,6aR)-2-oxohexahydro-1H-thieno[3,4-d]imidazol-4-yl)), $Y^3$ is cycloalkyl, (heterocycloalkyl)alkyl, heterocycloalkyl, aryl, heteroaryl and $Y^4$ is alkyl, heterocycloalkyl or (heterocycloalkyl)alkyl. In some particular instances, $R^a$ is methyl, ethyl, heptyl, trifluoromethyl. Still in other instances, $Ar^1$ is selected from the group consisting of 4-chlorophenyl, 1-methyl-1H-imidazol-4-yl and 6-chloropyridin-3-yl. Yet in other instances $Y^3$ is selected from the group consisting of 4,4-difluorocyclohexyl, 4-chlorophenyl, (tetrahydro-2H-pyran-4-yl)methyl, 1-(2,2,2-trifluoroacetyl)

piperidin-4-yl, 1-(2,2,2-trifluoroacetyl)azetidin-3-yl, 6-chloropyridin-3-yl and (morpholino)methyl. Still in other instances, $Y^4$ is selected from the group consisting of methyl, tetrahydro-2H-pyran-4-yl and tetrahydrofuran-2-yl) methyl. In some embodiments, each of $R^x$, $R^y$ and $R^z$ is independently H, alkyl, cycloalkyl, heterocycloalkyl, (heterocycloalkyl)alkyl, or (cycloalkyl)alkyl. Still in other embodiments, each of $R^x$, $R^y$ and $R^z$ is independently H or alkyl. In one particular embodiment, $R^x$, $R^y$ and $R^z$ are H.

Another aspect of the invention provides a compound of the formula:

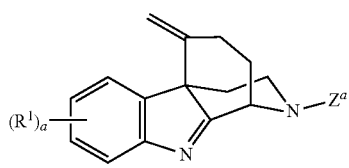

B where a is 0, 1 or 2; each $R^1$ is independently halide, alkyl or alkoxide; and $Z^a$ is hydrogen, a nitrogen protecting group, a moiety of the formula —C(=O)$Y^a$ or a moiety of the formula —SO$_2$$Y^b$, wherein $Y^a$ is haloalkyl, alkyl, (heterocycloalkyl)alkyl, heteroalkyl, heterocycloalkyl or heteroaryl, and $Y^b$ is heteroaryl.

With regards to compound of Formula B, in some embodiments, a is 0 or 1. Still in other embodiments, $R^1$ is halide or alkoxide. Yet in other embodiments, $Z^a$ is selected from the group consisting of hydrogen, —COAr$^1$, Ns, —SO$_2$Ar$^1$, Ts, Cbz and COCF$_3$, where Ar$^1$ is optionally substituted phenyl. Still yet in other embodiments, $Y^a$ is selected from the group consisting of (tetrahydro-2H-pyran-4-yl)methyl, a moiety of the formula —CH$_2$NHC(=O)OtBu, 1-methylpiperidin-4-yl, (morpholino)methyl, pyridin-3-yl, 6-chloro-pyridin-3-yl, 4-methylpiperazin-1-yl, 2-methyloxazol-4-yl. Still in further embodiments, $Y^b$ is 1-methyl-1H-imidazol-4-yl.

It should be appreciated that combinations of various groups described herein form other preferred embodiments. In this manner, a variety of compounds of Formulas A and B are embodied within the present invention.

Another aspect of the invention provides an antibiotic composition comprising one or more of a compound of the invention described herein. In some embodiments, the antibiotic composition further comprises a β-lactam antibiotic. Exemplary β-lactam antibiotics include β-lactam comprises amoxicillin, clavulanic acid, cefazolin, meropenem, and a combination thereof. Yet in other embodiments, the antibiotic composition further comprises a β-lactamase inhibitor or other resistance-modifying agent or a combination thereof.

Compounds of the invention are useful in treating bacterial infection in a subject. In some embodiments, compounds of the invention are used to treat drug resistant strain bacterial infection. Yet in other embodiments, the compound of the invention is used to treat MRSA infection.

Yet another aspect of the invention provides a method for producing a fused-azaindoline compound of the formula:

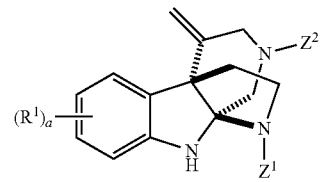

IA said method comprising contacting a substituted indole compound of the formula:

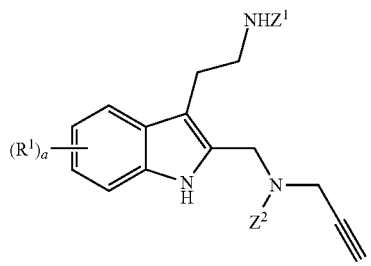

with a gold catalyst under conditions sufficient to produce the fused-azaindoline compound of Formula IA, where a is 1 or 2; each of $R^1$ is independently halide; and each of $Z^1$ and $Z^2$ is independently hydrogen, alkyl or a nitrogen protecting group. In some embodiments, the gold catalyst is Au(I)-containing organometallic complex. In one specific embodiment, the gold catalyst is Ph$_3$PAuNTf$_2$.

Terms "halide," "halogen" and "halo" are used interchangeably herein and refer to fluoro, chloro, bromo, or iodo.

The term "alkyl" refers to a saturated linear monovalent hydrocarbon moiety of one to twenty, typically one to fifteen, and often one to ten carbon atoms or a saturated branched monovalent hydrocarbon moiety of three to twenty, typically three to fifteen, and often three to ten carbon atoms. Exemplary alkyl group include, but are not limited to, methyl, ethyl, n-propyl, 2-propyl, tert-butyl, pentyl, iso-pentyl, hexyl, and the like.

"Alkylene" refers to a saturated linear divalent hydrocarbon moiety of one to twenty, typically one to fifteen and often one to ten carbon atoms or a branched saturated divalent hydrocarbon moiety of three to twenty, typically three to fifteen and often three to ten carbon atoms. Exemplary alkylene groups include, but are not limited to, methylene, ethylene, propylene, butylene, pentylene, and the like.

"Haloalkyl" refers to an alkyl group as defined herein in which one or more hydrogen atom is replaced by same or different halide atoms. Exemplary haloalkyls include, but are not limited to, —CH$_2$Cl, —CF$_3$, —CH$_2$CF$_3$, —CH$_2$CCl$_3$, and the like.

"Aryl" refers to a monovalent mono-, bi- or tricyclic aromatic hydrocarbon moiety of 6 to 15 ring atoms such as phenyl, naphthyl, etc. Aryl may be substituted with one or more, typically 1-3, and often 1 or 2 substituents. Exemplary substituents of aryl group include, but are not limited to, those substituents described for heteroaryl.

"Heteroaryl" means a monovalent monocyclic or bicyclic aromatic moiety of 5 to 12 ring atoms containing one, two, or three ring heteroatoms selected from N, O, or S, the remaining ring atoms being C. The heteroaryl ring can be substituted with one or more substituents, typically one or more, often one to four, and more often one or two substituents. Suitable substituents include alkyl, haloalkyl, heteroalkyl, heterocyclyl, halo, nitro, cyano, carboxy, acyl, -(alkylene)$_n$-COOR (where n is 0 or 1 and R is hydrogen, alkyl, optionally substituted phenylalkyl, or optionally substituted heteroaralkyl), or -(alkylene)$_n$-CONR$^a$R$^b$ (where n is 0 or 1, and R$^a$ and R$^b$ are, independently of each other, hydrogen, alkyl, cycloalkyl, cycloalkylalkyl, hydroxyalkyl, aryl, or R$^a$ and R$^b$ together with the nitrogen atom to which they are attached form a heterocyclyl ring). More specifically the term heteroaryl includes, but is not limited to, pyridyl, furanyl, thiophenyl, thiazolyl, isothiazolyl, triazolyl, imidazolyl, isoxazolyl, pyrrolyl, pyrazolyl, pyrazinyl, pyrimidinyl, benzofuranyl, isobenzofuranyl, benzothiazolyl, benzoisothiazolyl, benzotriazolyl, indolyl, isoindolyl, benzoxazolyl, quinolyl, isoquinolyl, benzimidazolyl, benzisoxazolyl, benzothiophenyl, dibenzofuran, and benzodiazepin-2-one-5-yl, and the like.

"Heterocycloalkyl" refers to a non-aromatic mono- or bicyclic moiety of three to twelve ring atoms in which one or more, typically one or two ring atoms are heteroatoms selected from N, O, or S(O)$_n$ (where n is an integer from 0 to 2), the remaining ring atoms being C, where one or two C atoms can optionally be a carbonyl group. The heterocycloalkyl ring can be optionally substituted independently with one or more, typically one, two, or three, substituents. When two or more substituents are present in a heterocycloalkyl, each substituent is independently selected. Exemplary substituents for heterocycloalkyl include, but are not limited to, alkyl, haloalkyl, heteroalkyl, halo, nitro, cyano, optionally substituted phenyl, optionally substituted heteroaryl, optionally substituted phenylalkyl, optionally substituted heteroaralkyl, acyl, -(alkylene)$_n$-COOR (n is 0 or 1 and R is hydrogen, alkyl, optionally substituted phenyl, optionally substituted phenylalkyl, or optionally substituted heteroaralkyl), or -(alkylene)$_n$CONR$^a$R$^b$ (where n is 0 or 1, and R$^a$ and R$^b$ are, independently of each other, hydrogen, alkyl, cycloalkyl, cycloalkylalkyl, hydroxyalkyl, aryl, or R and R' together with the nitrogen atom to which they are attached form a heterocyclyl ring). More specifically the term heterocyclo includes, but is not limited to, tetrahydropyranyl, piperidino, piperazino, morpholino, thiomorpholino, thiomorpholino-1-oxide, thiomorpholino-1,1-dioxide, and the like.

"(Heterocycloalkyl)alkyl" refers to a moiety of the formula —R$^a$R$^b$, where R$^b$ is heterocycloalkyl and R$^a$ is alkylene as defined herein.

"Alkynyl" means a linear monovalent hydrocarbon moiety of two to ten carbon atoms or a branched monovalent hydrocarbon moiety of three to ten carbon atoms, containing at least one carbon-carbon triple bond, e.g., ethenyl, propenyl, and the like.

"Heteroalkyl" means a branched or unbranched, cyclic or acyclic saturated alkyl moiety containing carbon, hydrogen and one or more heteroatoms in place of a carbon atom, or optionally one or more heteroatom-containing substituents independently selected from =O, —OR$^a$, —C(O)R$^a$, —NR$^b$R$^c$, —C(O)NR$^b$R$^c$ and —S(O)$_n$R$^d$ (where n is an integer from 0 to 2). R$^a$ is hydrogen, alkyl, haloalkyl, cycloalkyl, cycloalkylalkyl, heterocyclyl, heterocyclylalkyl, aryl, aralkyl, heteroaryl, heteroaralkyl, or acyl. R$^b$ is hydrogen, alkyl, haloalkyl, cycloalkyl, cycloalkylalkyl, heterocyclyl, heterocyclylalkyl, aryl, aralkyl, heteroaryl, heteroaralkyl, or acyl. R$^c$ is hydrogen, alkyl, haloalkyl, cycloalkyl, cycloalkylalkyl, heterocyclyl, heterocyclylalkyl, aryl, aralkyl, acyl, alkyl sulfonyl, carboxamido, or mono- or di-alkylcarbomoyl. Optionally, R$^b$ and R$^c$ can be combined together with the nitrogen to which each is attached to form a four-, five-, six- or seven-membered heterocyclic ring (e.g., a pyrrolidinyl, piperidinyl or morpholinyl ring). R$^d$ is hydrogen (provided that n is 0), alkyl, haloalkyl, cycloalkyl, cycloalkylalkyl, heterocyclyl, heterocyclylalkyl, aryl, aralkyl, heteroaryl, heteroaralkyl, acyl, amino, monsubstituted amino, disubstituted amino, or hydroxyalkyl. Representative examples of heteroalkyls include, but are not limited to, 2-methoxyethyl, benzyloxymethyl, thiophen-2-ylthiomethyl, 2-hydroxyethyl, 2,3-dihydroxypropyl, and guanidine derivative of the formula —C(=NR$^a$)—NR$^b$R$^c$ where each of R$^a$, R$^b$ and R$^c$ is independently H, alkyl, cycloalkyl, heterocycloalkyl, (heterocycloalkyl)alkyl, (cycloalkyl)alkyl, and heteroalkyl.

"Acyl" refers to a moiety of the formula —C(O)R', where R' is alkyl, haloalkyl, aryl, or aralkyl. "Sulfonyl" refers to a moiety of the formula —S(O)$_2$R$^y$, where R$^y$ is alkyl, haloalkyl, optionally substitute aryl, optionally substituted aralkyl, or (cycloalkyl)alkyl. "Leaving group" has the meaning conventionally associated with it in synthetic organic chemistry, i.e., an atom or a group capable of being displaced by a nucleophile and includes halo (such as chloro, bromo, and iodo), alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, and the like.

"Pharmaceutically acceptable excipient" refers to an excipient that is useful in preparing a pharmaceutical composition that is generally safe, non-toxic and neither biologically nor otherwise undesirable, and includes excipient that is acceptable for veterinary use as well as human pharmaceutical use.

"Pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

The terms "pro-drug" and "prodrug" are used interchangeably herein and refer to a pharmacologically substantially inactive derivative of a parent drug molecule that requires biotransformation, either spontaneous or enzymatic, within the organism to release the active drug. Prodrugs are variations or derivatives of the compounds of this invention which have groups cleavable under metabolic conditions. Prodrugs become the compounds of the invention which are pharmaceutically active in vivo when they undergo solvolysis under physiological conditions or undergo enzymatic degradation. Prodrug compounds of this invention may be called single, double, triple etc., depending on the number of biotransformation steps required to release the active drug within the organism, and indicating the number of functionalities present in a precursor-type form. Prodrug forms often offer advantages of solubility, tissue compatibility, or delayed release in the mammalian organism (see, Bundgard, *Design of Prodrugs*, pp. 7-9, 21-24, Elsevier, Amsterdam 1985 and Silverman, *The Organic Chemistry of Drug Design and Drug Action*, pp. 352-401, Academic Press, San Diego, Calif., 1992). Prodrugs commonly known in the art include acid derivatives that are well known to one skilled in the art, such as, but not limited to, esters prepared by reaction of the parent acids with a suitable alcohol, or amides prepared by reaction of the parent acid compound with an amine, or basic groups reacted to form an acylated base derivative.

"Protecting group" refers to a moiety, except alkyl groups, that when attached to a reactive group in a molecule masks, reduces or prevents that reactivity. Examples of protecting groups can be found in T. W. Greene and P. G. M. Wuts, *Protective Groups in Organic Synthesis*, 3$^{rd}$ edition, John Wiley & Sons, New York, 1999, and Harrison and Harrison et al., *Compendium of Synthetic Organic Methods*, Vols. 1-8 (John Wiley and Sons, 1971-1996), which are incorporated herein by reference in their entirety. Representative amino or amine protecting groups include, formyl, acyl groups (such as acetyl, trifluoroacetyl, and benzoyl), benzyl, alkoxycarbonyl (such as benzyloxycarbonyl (CBZ), and tert-butoxycarbonyl (Boc)), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), sulfonyl, and the like.

"A therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated. "Treating" or "treatment" of a disease includes: (1) preventing the disease, i.e., causing the clinical symptoms of the disease not to develop in a mammal that may be exposed to or predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms.

When describing a chemical reaction, the terms "treating", "contacting" and "reacting" are used interchangeably herein, and refer to adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product. As used herein, the terms "those defined above" and "those defined herein" when referring to a variable incorporates by reference the broad definition of the variable as well as any narrow definitions, if any.

Composition

Another aspect of the invention provides an antibiotic composition comprising a compound of the invention that is capable of re-sensitizing the susceptibility of methicillin-resistant *S. aureus* to said β-lactam antibiotic. In some embodiments, the antibiotic composition further includes a β-lactam antibiotic. Suitable β-lactam antibiotics are well known to one skilled in the art, and exemplary β-lactam antibiotics can be found in Merck Index, 15$^{th}$ Ed., Edited by Maryadele J O'Neil, Royal Society of Chemistry, 2013, and Physicians' Desk Reference (i.e., "PDR") 67$^{th}$ Ed., 2013, all of which are incorporated herein by reference in their entirety. In some embodiments, the antibiotic composition comprises an indoline and/or indolenine alkaloid compound described herein.

The compounds of the invention can be administered to a patient or a subject to achieve a desired physiological effect. Generally, the patient is an animal, typically a mammal, and often a human. The compound can be administered in a variety of forms adapted to the chosen route of administration, i.e., orally or parenterally. Parenteral administration in this respect includes administration by the following routes: intravenous; intramuscular; subcutaneous; intraocular; intrasynovial; transepithelially including transdermal, ophthalmic, sublingual and buccal; topically including ophthalmic, dermal, ocular, rectal and nasal inhalation via insufflation and aerosol; intraperitoneal; and rectal systemic.

The active compound can be orally administered, for example, with an inert diluent or with an assimilable edible carrier, or it can be enclosed in hard or soft shell gelatin capsules, or it can be compressed into tablets, or it can be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparation can contain at least 0.1% of active compound. The percentage of the compositions and preparation can, of course, be varied and can conveniently be between about 1 to about 10% of the weight of the unit. The amount of active compound in such therapeutically useful compositions is such that a suitable dosage will be obtained. Typical compositions or preparations according to the invention are prepared such that an oral dosage unit form contains from about 1 to about 1000 mg of active compound.

The tablets, troches, pills, capsules and the like can also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin can be added or a flavoring agent such as peppermint, oil of wintergreen, or cherry flavoring. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar or both. A syrup or elixir can contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound can be incorporated into sustained-release preparations and formulation. In addition to the common dosage forms set out above, the compounds of the invention may also be administered by controlled release means and/or delivery devices capable of releasing the active ingredient (prenylation inhibitor) at the required rate to maintain constant pharmacological activity for a desirable period of time. Such dosage forms provide a supply of a drug to the body during a predetermined period of time and thus maintain drug levels in the therapeutic range for longer periods of time than conventional non-controlled formulations. Examples of controlled release pharmaceutical compositions and delivery devices that may be adapted for the administration of the active ingredients of the present invention are described in U.S. Pat. Nos.: 3,847,770; 3,916,899; 3,536,809; 3,598,123; 3,630,200; 4,008,719; 4,687,610; 4,769,027; 5,674,533; 5,059,595; 5,591,767; 5,120,548; 5,073,543; 5,639,476; 5,354,566; and 5,733,566, the disclosures of which are hereby incorporated by reference.

Pharmaceutical compositions for use in the methods of the present invention may be prepared by any of the methods of pharmacy, but all methods include the step of bringing the active ingredient into association with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet may be prepared by compression or molding, optionally with one or more accessory ingredients. Compressed tablets may be prepared by compressing in a suitable machine the active ingredient in a free-flowing form such as powder or granules, optionally mixed with a binder, lubricant, inert diluent, surface active or dispersing agent. Molded tablets may be made by molding, in a suitable machine, a mixture of the powdered compound moistened with an inert liquid diluent.

The active compound can also be administered parenterally. Solutions of the active compound as a free base or pharmacologically acceptable salt can be prepared in water suitably mixed with a surfactant such as hydroxypropylcellulose. Dispersion can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It can be stable under the conditions of manufacture and storage and must be preserved against the contaminating action of microorganisms such as bacterial and fungi. The carrier can be a solvent of dispersion medium containing, for example, water, ethanol, polyol (e.g., glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, e.g., sugars or sodium chloride. Prolonged absorption of the injectable compositions of agents delaying absorption, e.g., aluminum monostearate and gelatin.

Sterile injectable solutions are prepared by incorporating the active compound in the required amount in the appropriate solvent with various other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique which yield a powder of the active ingredient plus any additional desired ingredient from previously sterile-filtered solution thereof.

The compounds of the invention can be administered to a mammal alone or in combination with pharmaceutically acceptable carriers, as noted above, the proportion of which is determined by the solubility and chemical nature of the compound, chosen route of administration and standard pharmaceutical practice.

The physician can readily determine the dosage of the present therapeutic agents which will be most suitable for prophylaxis or treatment and it will vary with the form of administration and the particular compound chosen, and also, it will vary with the particular patient under treatment. The physician will generally wish to initiate treatment with small dosages by small increments until the optimum effect under the circumstances is reached. The therapeutic dosage can generally be from about 0.1 to about 1000 mg/day, and preferably from about 10 to about 100 mg/day, or from about 0.1 to about 50 mg/Kg of body weight per day and preferably from about 0.1 to about 20 mg/Kg of body weight per day and can be administered in several different dosage units. Higher dosages, on the order of about 2× to about 4×, may be required for oral administration.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

EXAMPLES

Various experimental procedures used herein are similar to those described in a commonly assigned PCT Patent Application No. PCT/US14/32585, filed Apr. 1, 2014, which is incorporated herein by reference in its entirety.

Example 1: Polycyclic Indoline Compounds

The present inventors have found that compounds of formula 2 have a significantly lower cLogD$_{7.4}$ relative to the carbon analog in which the nitrogen on the six-membered ring is replaced with a carbon atom, thereby increasing its bioavailability. The tricyclic indoline core structure can be transformed into a piperidine-fused indoline or aza-tricyclic indoline (ATI).

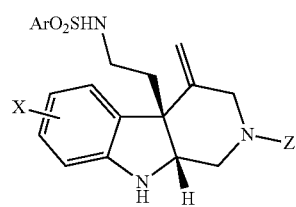

2

(e.g., Ar=4-chlorophenyl, 4-nitrophenyl, 4-chloro-2-nitrophenyl, 4-methylphenyl, etc., and Z is Ar, methylsulfonate, trifluoroacetate, —CH$_2$CO$_2$H, etc.) ATIs can be further modified at the c-ring nitrogen (i.e., "Z") to further decrease the cLogD$_{7.4}$. In addition, the ATI is a common motif in many biologically active indole alkaloid natural products (e.g., ajmaline and reserpine). These discoveries led the present inventor's investigation into using ATIs RMAs, antibiotics or both.

Synthesis of ATIs utilized a gold- or platinum-catalyzed cyclization of a propargyl amine-conjugated tryptamine derivative 8 as shown below to form the aza-tetracyclic indolines 9, which can further undergo a ring-opening reduction to produce the desired ATIs 2.

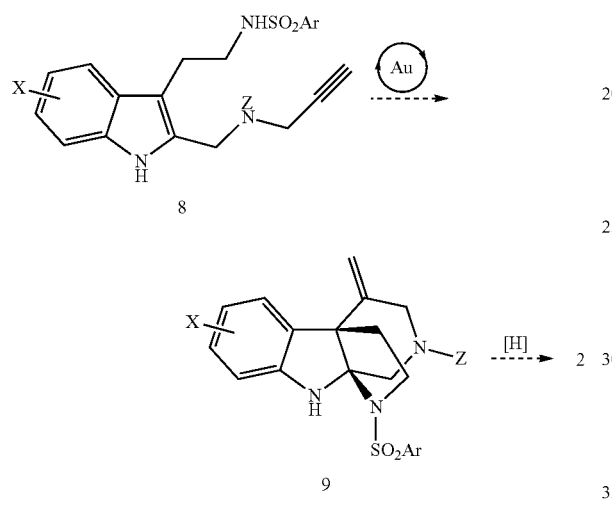

These ATIs can be further modified to introduce functional groups that can improve pharmacokinetics and physical properties without sacrificing anti-MRSA activity. Synthesis of compound 2 was based on a discovery by the present inventor of at least in part a highly efficient gold- (or platinum) catalyzed tandem cyclization.

Compound 8 can be prepared by, for example, one-pot, three-component reaction using imine 3 to give 2-methyl tryptamine derivative 7 as shown below.

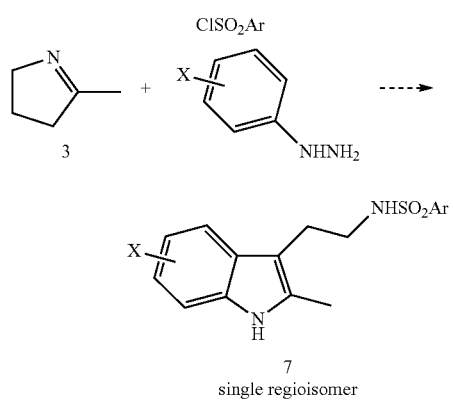

Protection of both nitrogen groups (e.g., using Boc-protecting group) followed by selective bromination of the methyl group of compound 7a (where X is 5-bromo-7-fluoro and Ar is 4-chlorophenyl), e.g., through a radical bromination, provided bromide compound 10a.

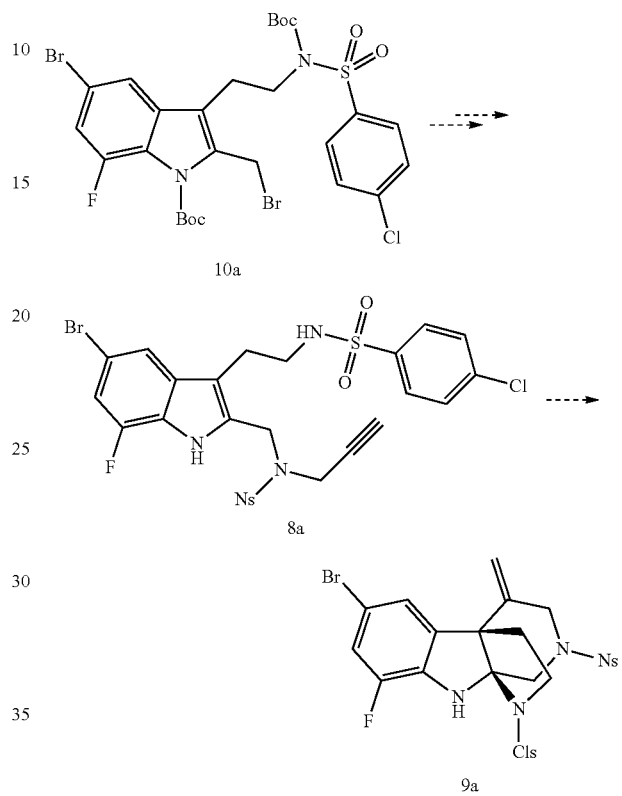

Compound 10a was then alkylated using propargyl amine. Deprotection of both Boc groups using trifluoroacetic acid (TFA) followed by protection of the secondary amine nitrogen with 4-nitrobenzesulfonyl (Ns) group provided the cyclization precursor 8a. Using this synthetic strategy, a number of cyclization precursors with a variety of different substitutions were synthesized in good yield.

With cyclization precursor 8a a tandem cyclization reaction was developed to produce the desired tetracyclic indoline compound 9a using a variety of catalysts and reaction conditions as shown in Table 1-1.

TABLE 1-1

Tandem cyclization reaction conditions and yields.

| Entry | Catalyst (5 mol %) | Solvent | T [° C.] | Yield [%] |
|---|---|---|---|---|
| 1 | Ph$_3$PAuNTf$_2$ | Toluene | 60 | 22 |
| 2 | Ph$_3$PAuNTf$_2$ | Toluene | 90 | 43 |
| 3 | PtCl$_2$ | Toluene | 90 | <10 |
| 4 | PtCl$_4$ | Toluene | 90 | 0 |
| 5 | H$_2$PtCl$_6$•6H$_2$O | Toluene | 90 | <10 |
| 6 | IPrAuCl | Toluene | 90 | 0 |
| 7 | IPrAuCl/AgSbF$_6$ | Toluene | 90 | 11 |
| 8 | XPhosAuNTf$_2$ | Toluene | 90 | 61 |
| 9 | XPhosAuNTf$_2$ | 1,4-Dioxane | 90 | 97 |

TABLE 1-1-continued

Tandem cyclization reaction conditions and yields.

Entry  Catalyst (5 mol %)  Solvent  T [° C.]  Yield [%]

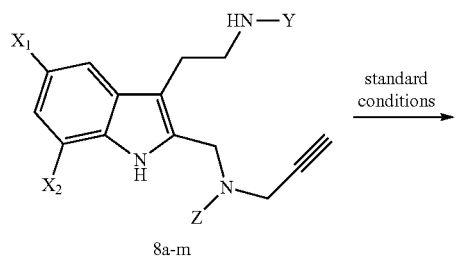

Other additional cyclization precursors were prepared using a similar synthetic approach to produce compounds 8b-m, which were cyclized to the corresponding compounds 9a-m as shown in Table 1-2.

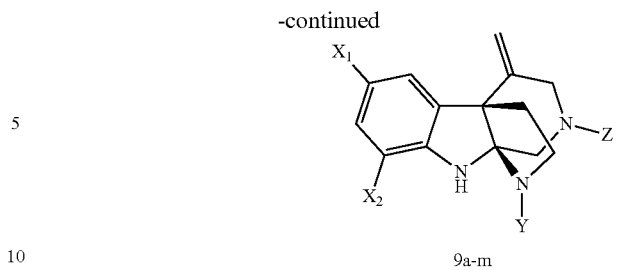

TABLE 1-2

| Entry | 8 | $X^1$ | $X^2$ | Y | Z | Yield [%] [b] |
|---|---|---|---|---|---|---|
| 1 | 8a | Br | F | Cls | Ns | 97 |
| 2 | 8b | Br | F | Cls | Tfa | 72 |
| 3 | 8c | Br | F | Cls | Ms | 90 |
| 4 | 8d | Br | F | Cls | CNs | 91 [c] |
| 5 | 8e | Br | F | Cls | Ts | 96 |
| 6 | 8f | Br | F | Cls | Cbz | 71 |
| 7 | 8g | Br | H | Cls | Ns | 92 [d] |
| 8 | 8h | Cl | H | Cbz | Ns | 96 [e] |
| 9 | 8i | Cl | Cl | Cbz | Ns | 95 [e] |
| 10 | 8j | F | H | Cbz | Ns | 91 [e] |
| 11 | 8k | Cl | H | Cbz | Tfa | 90 [f] |
| 12 | 8l | Cl | H | Cls | Tfa | 89 [e] |
| 13 | 8m | Cl | H | COOMe | Tfa | 91 [f] |

[a] Standard reaction conditions (5 mol % XPhosAuNTf$_2$, 1,4-dioxane, 90° C., 12 hours unless noted otherwise.
[b] Isolated yield based on complete conversion of substrate.
[c] 10 mol % catalyst used.
[d] 2 hour reaction time.
[e] 2 hour reaction time at 60° C.
[f] 30 minute reaction time at 60° C.
[g] Cls, 4-chloro-benzensulfonyl; Ns, 4-nitro-benzenesulfonyl; Tfa, trifluoroacetyl; Ms, methanesulfonyl; CNs, 4-chloro-2-nitro-benzenesulfonyl; Ts, 4-methyl-benzensulfonyl; Cbz, benzyloxycarbonyl.

To explore ATIs with unique physical properties, the cyclization products 9a-c, were converted to ATIs using reductive ring-opening conditions to furnish 11a-c as shown in Scheme 1-1.

Scheme 1-1 Synthesis of ATIs.

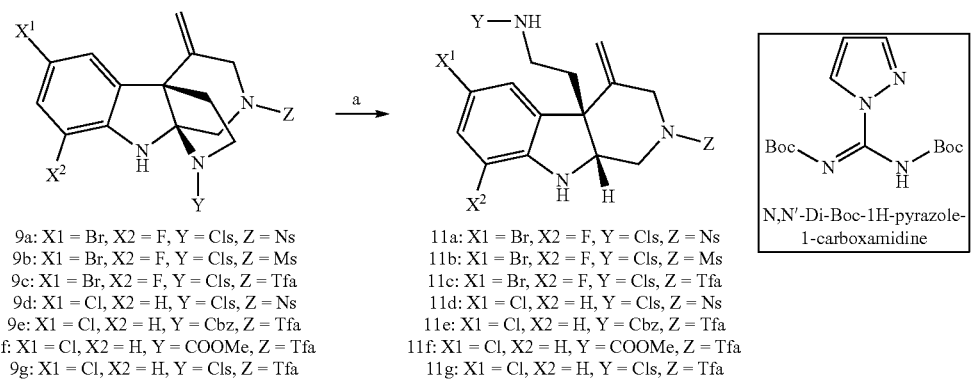

9a: X1 = Br, X2 = F, Y = Cls, Z = Ns
9b: X1 = Br, X2 = F, Y = Cls, Z = Ms
9c: X1 = Br, X2 = F, Y = Cls, Z = Tfa
9d: X1 = Cl, X2 = H, Y = Cls, Z = Ns
9e: X1 = Cl, X2 = H, Y = Cbz, Z = Tfa
9f: X1 = Cl, X2 = H, Y = COOMe, Z = Tfa
9g: X1 = Cl, X2 = H, Y = Cls, Z = Tfa

11a: X1 = Br, X2 = F, Y = Cls, Z = Ns
11b: X1 = Br, X2 = F, Y = Cls, Z = Ms
11c: X1 = Br, X2 = F, Y = Cls, Z = Tfa
11d: X1 = Cl, X2 = H, Y = Cls, Z = Ns
11e: X1 = Cl, X2 = H, Y = Cbz, Z = Tfa
11f: X1 = Cl, X2 = H, Y = COOMe, Z = Tfa
11g: X1 = Cl, X2 = H, Y = Cls, Z = Tfa

N,N'-Di-Boc-1H-pyrazole-1-carboxamidine

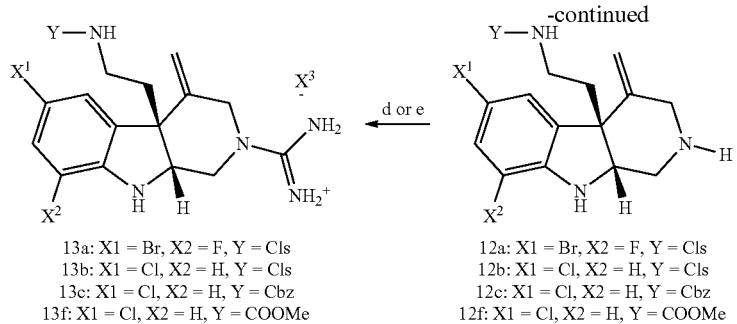
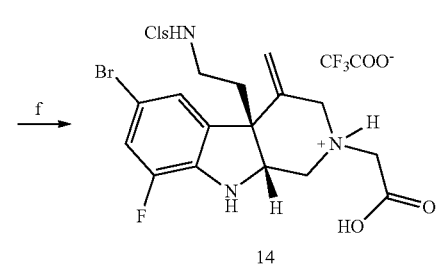

13a: X1 = Br, X2 = F, Y = Cls
13b: X1 = Cl, X2 = H, Y = Cls
13c: X1 = Cl, X2 = H, Y = Cbz
13f: X1 = Cl, X2 = H, Y = COOMe

12a: X1 = Br, X2 = F, Y = Cls
12b: X1 = Cl, X2 = H, Y = Cls
12c: X1 = Cl, X2 = H, Y = Cbz
12f: X1 = Cl, X2 = H, Y = COOMe

14

X3 = Cl⁻ or CF₃CO₂⁻

Reagents and conditions: (a) TFA, NaCNBH₃, THF/MeOH, 0° C.; (b) PhSH, K₂CO₃, CH₃CN, 60° C.; (c) K2CO3, MeOH, THF, H2O; d) i. 15, CH₂Cl₂, 23° C.; ii. TFA, CH₂Cl₂, 0° C.; (e) i. N,N'-Di-Boc-1H-pyrazole-1-carboxamidine, CH₂Cl₂, 23° C.; ii. HCl Conc., THF, 0° C. (f) i. Tert-butyl bromoacetate, Et₃N, CH₂Cl₂, 0° C.; ii. TFA, CH₂Cl₂, 0° C. Tfa, trifluoroacetamide; TFA, trifluoroacetic acid; Cls, 4-chlorobenzenesulfonyl.

To synthesize additional ATIs with even lower clogD$_{7.4}$ values, the Ns group of 11a was removed to afford secondary amine 12. The secondary amine was then functionalized as a cationic guanidine group 13 using a commercially available guanidinylation reagent 15 followed by deprotection with trifluoroacetic acid. A zwitterion analogue 14 was also synthesized by treating 12 with tert-butyl bromoacetate followed by deprotection with trifluoroacetic acid.

Without being bound by any theory, it is believed that introducing ionizable groups to the ATI core would: 1) decrease off-target mammalian toxicity, 2) improve metabolic stability and/or 3) improve RMA activity in MRSA. In addition to controlling distribution in mammalian cells, adding charge to ATIs may also decrease general drug-metabolism.

ATIs 11-14 represent a wide range of clogD values and their minimum re-sensitizing concentrations (MRCS) for cefazolin (i.e., a first-generation cephalosporin) and amoxicillin/clavulanic acid (i.e., Augmentin, amox/clav) was evaluated as well as their minimum inhibitory concentrations (MICs) in a multi-drug resistant MRSA strain, ATCC BAA-44. The results are shown in Table 1-3. Any compounds with promising MRC and MIC were then evaluated for potential mammalian toxicity by determining their half growth inhibitory concentrations (GI$_{50}$) in human cervical adenocarcinoma (HeLa) cells.

TABLE 1-3

Comparison of the biological activity of Ofl and ATIs.

| Compound | clogD$_{7.4}$ | MRC Cef [a] | MRC Amox/clav [a] | MIC [a] | GI$_{50}$ [a], [b] |
|---|---|---|---|---|---|
| Ns-ATI 11a | 4.5 | >32 | >32 | >32 | NT |
| Ms-ATI 11b | 4.1 | >32 | >32 | >32 | NT |
| TFA-ATI 11c | 2.5 | 4 | 4 | >32 | 19 |
| NH-ATI 12 | 2.0 | 4 | 4 | 8 | 6.7 |
| Guan-ATI 13 | 0.74 | 2 | 2 | 8 | 40 |
| Gly-ATI 14 | 0.54 | >32 | >32 | >32 | NT |

[a] All MIC, MRC, and GI$_{50}$ values are in µg mL$^{-1}$;
[b] Determined for HeLa cells.
Cef—cefazolin; amox/clav—amoxicillin/clavulanic acid; NT—Not tested.

Compound 11c potentiated the activity of β-lactams in BAA-44 without observable antibacterial activity. The more polar analogue, amine 12, exhibited potent antibacterial activity on its own. The guanidine analogue 13 showed not only improved β-lactam-potentiating activity (MRCs=2 µg mL$^{-1}$ for both cefazolin and amox/clav) with moderate antibacterial activity (MIC=8 µg mL$^{-1}$), but also much lower mammalian toxicity with the GI$_{50}$ of 40 µg mL$^{-1}$ in HeLa cells. Compound 14 is zwitterionic under physiological conditions and has even lower clogD value. Further evaluations of 13 in a variety of MRSA strains, such as community-acquired MRSA strains NRS-100 and NRS-384, and vancomycin-resistant S. aureus (VRSA) strain NR-46414, also gave a similar results (MRCs=2 µg mL$^{-1}$).

ATI 12 was treated with sulfonyl chlorides, acyl chlorides, chloroformates, and succimidyl esters to give ATI analogues 15a-g, 16a-u (Scheme 1-2).

Scheme 1-2 Synthesis of Acyl-ATIs.

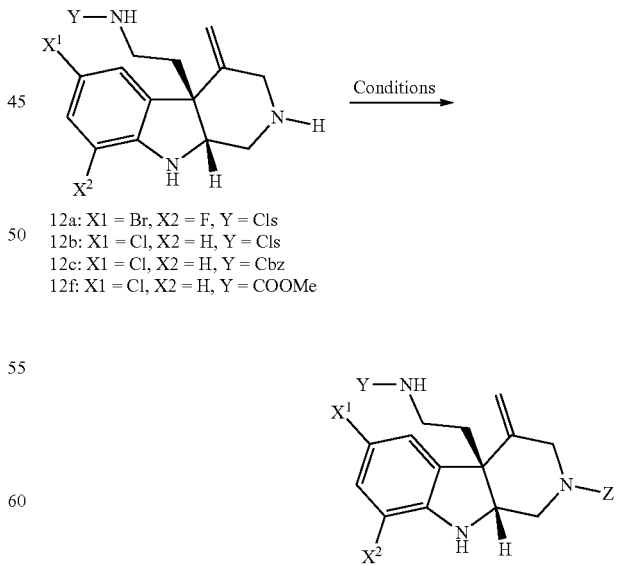

12a: X1 = Br, X2 = F, Y = Cls
12b: X1 = Cl, X2 = H, Y = Cls
12c: X1 = Cl, X2 = H, Y = Cbz
12f: X1 = Cl, X2 = H, Y = COOMe 15a-g: X1 = Br, X2 = F, Y = Cls
16a-p: X1 = Cl, X2 = H, Y = Cls
16q-s: X1 = Cl, X2 = H, Y = Cbz
16t-u: X1 = Cl, X2 = H, Y = COOMe

-continued

Reagents and Conditions: (a) succimidyl ester, TEA, DCM; (b) TFA:DCM (1:1).
15a (Z = —C(=O)CH₃);
15b (Z = —C(=O)(CH₂)₂CCH);
15c (Z = —C(=O)CH₂NHC(=O)OtBu); CH);
15d (Z = —C(=O)CH₂NH₃⁺·OC(=O)CF₃);
15e (Z = —C(=O)(CH₂)₅NHC(=O)—CH₂CH₂Y¹);
15f (Z = —C(=O)(CH₂)₃Y²);
15g (Z = —C(=O)(CH₂)₂CO₂H);
16a (Z = —C(=O)CF₃);
16b (Z = —C(=O)CH₃);
16c (Z = —C(=O)CH₂CH₃);
16d (Z = —C(=O)(CH₂)₂CCH);
16e (Z = —C(=O)(CH₂)₆CH₃);
16f (Z = —C(=O)(4,4-difluorocyclohexyl));
16g (Z = —C(=O)CH₂((tetrahydro-2H-pyran-4-yl));
16h (Z = —C(=O)(1-(2,2,2-trifluoroacetyl)piperidin-4-yl));
16i (Z = —C(=O)(1-(2,2,2-trifluoroacetyl)azetidin-3-yl));
16j (Z = —C(=O)(4-chlorophenyl));

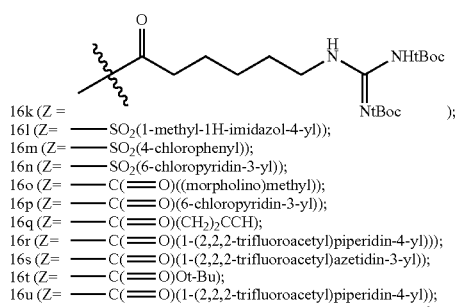

16k (Z = [structure shown]);
16l (Z= —SO₂(1-methyl-1H-imidazol-4-yl));
16m (Z= —SO₂(4-chlorophenyl));
16n (Z= —SO₂(6-chloropyridin-3-yl));
16o (Z= —C(=O)((morpholino)methyl));
16p (Z= —C(=O)(6-chloropyridin-3-yl));
16q (Z= —C(=O)(CH₂)₂CCH);
16r (Z= —C(=O)(1-(2,2,2-trifluoroacetyl)piperidin-4-yl));
16s (Z= —C(=O)(1-(2,2,2-trifluoroacetyl)azetidin-3-yl));
16t (Z= —C(=O)Ot-Bu);
16u (Z= —C(=O)(1-(2,2,2-trifluoroacetyl)piperidin-4-yl));

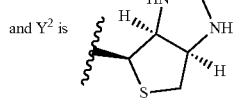

16v (Z= —SO₂(4-chlorophenyl)), where Y¹ is [structure];

and Y² is [structure].

The secondary amine 12b can be functionalized as different substituted ureas by treating with 1,1'-carbonyldiimidazole-activated-amines. Scheme 1-3.

Scheme 1-3. Synthesis of Urea-ATIs.

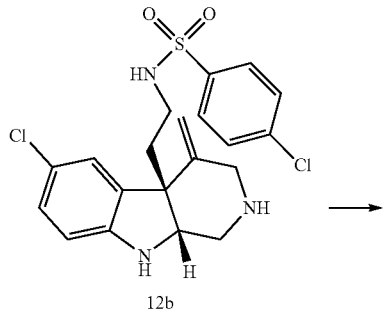

12b

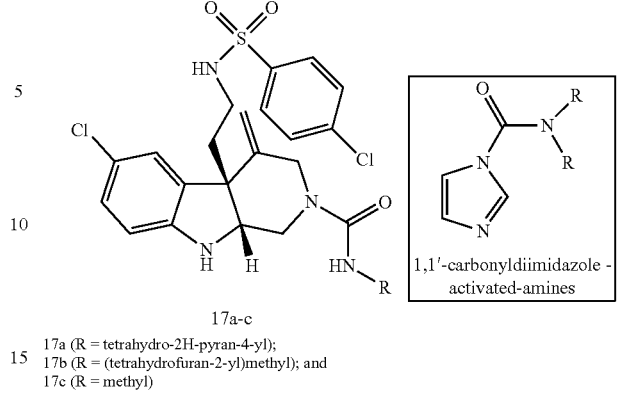

17a-c
17a (R = tetrahydro-2H-pyran-4-yl);
17b (R = (tetrahydrofuran-2-yl)methyl); and
17c (R = methyl)

Trifluoracetamide analogues with different substitution on the side chain were also prepared from 11d by removal of Cbz protecting group followed by treatment with sulfonyl chlorides, acyl chlorides, chloroformates, isocyanates, and 1,1'-carbonyldiimidazole activated amines to give sulfonamides, amides, carbamates, and ureas, respectively. Scheme 1-4.

Scheme 1-4 Synthesis of TFA-ATI analogues.

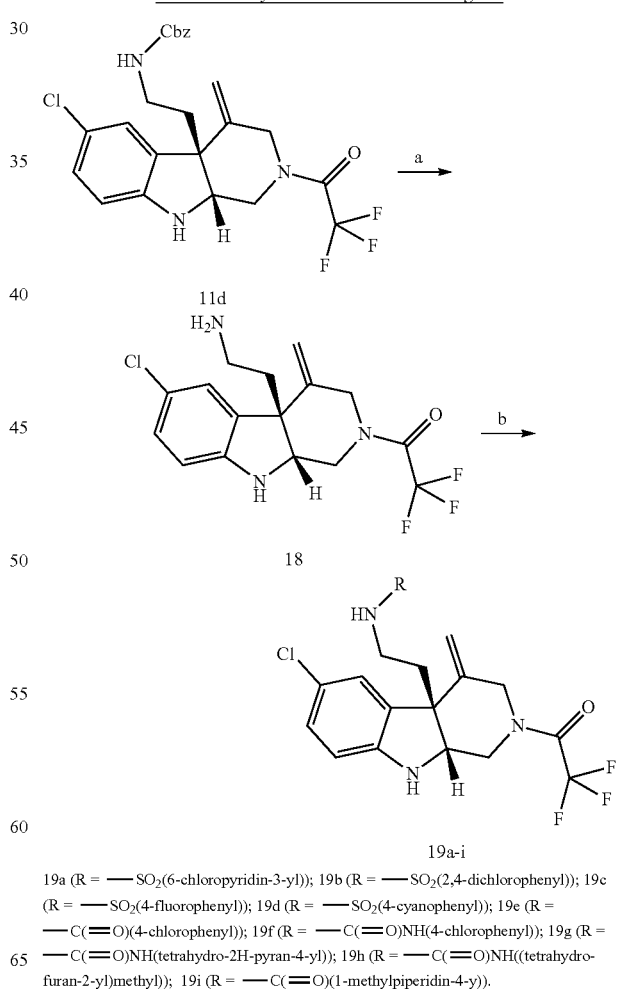

19a-i
19a (R = —SO₂(6-chloropyridin-3-yl)); 19b (R = —SO₂(2,4-dichlorophenyl)); 19c (R = —SO₂(4-fluorophenyl)); 19d (R = —SO₂(4-cyanophenyl)); 19e (R = —C(=O)(4-chlorophenyl)); 19f (R = —C(=O)NH(4-chlorophenyl)); 19g (R = —C(=O)NH(tetrahydro-2H-pyran-4-yl)); 19h (R = —C(=O)NH((tetrahydrofuran-2-yl)methyl)); 19i (R = —C(=O)(1-methylpiperidin-4-y)).

-continued

Reagents and Conditions: a) BF$_3$-diethyl etherate, dimethyl sulfide, DCM, 0° C.; b) sulfonyl chloride and TEA, acyl chloride and TEA, chloroformate and TEA, isocyanate or 1,1′-carbonyldiimidazole-activated-amine, DCM.

Trifluoroacetamide analogues 19a-f were deprotected to give secondary amine analogues 20a-f. Scheme 1-5.

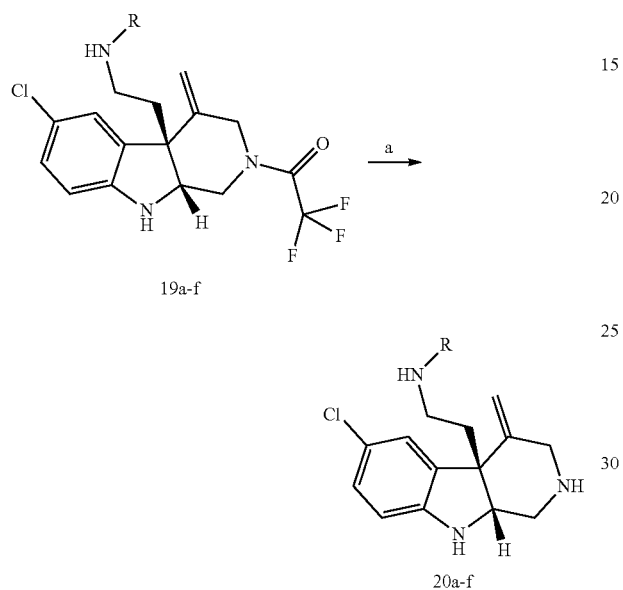

Scheme 1-5. Synthesis of NH-ATIs.

19a-f 20a-f

Reagents and Conditions: a) K$_2$CO$_3$, MeOH/H$_2$O (10:1).

Secondary amines 20a-f were treated with N,N-di-Boc-1H-pyrazole-1-carboxamidine followed by deprotection with trifluoracetic acid to give guanidine analogs 21a-f. Scheme 1-6.

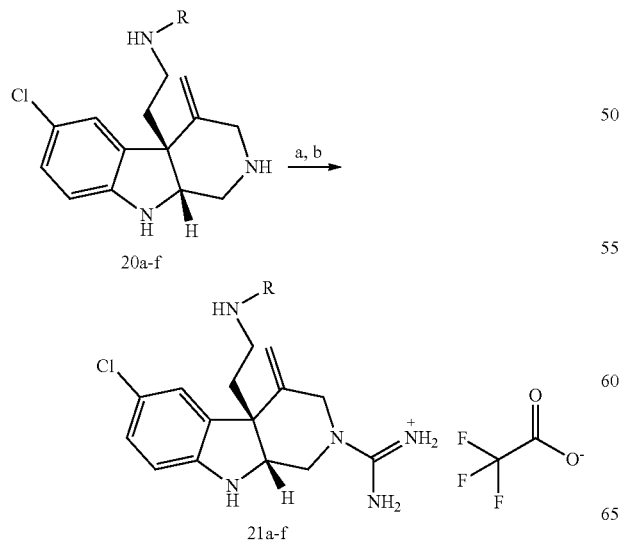

Scheme 1-6. Synthesis of Guan-ATIs.

20a-f 21a-f

-continued

Reagents and Conditions: a) N,N-di-Boc-1H-pyrazole-1-carboxamidine, DCM; b) TFA:DCM (1:1).

Functional groups affixed to the side chain nitrogen was converted to the piperidine nitrogen of ATIs. For example, 4-chloro-benzene-sulfonamide was transferred to the piperidine ring of ATIs to produce 22. Scheme 1-7.

Scheme 1-7 Sidechain-Piperidine functional group swap for NH-ATI.

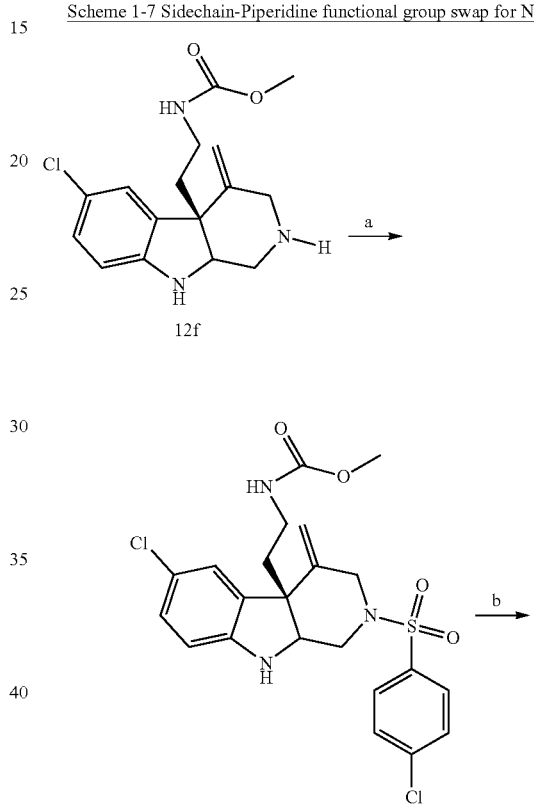

12f

16v

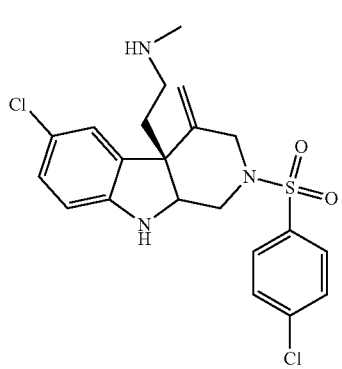

22

Reagents and Conditions: a) 4-chloro-benzene-sulfonyl chloride, TEA, DCM; b) lithium aluminum hydride, Reflux, THF, 6 hours.

The indoline nitrogen of ATIs could be modified with benzaldehydes through reductive amination. Scheme 1-8.

Scheme 1-8 Preparation of N-Benzyl ATIs.

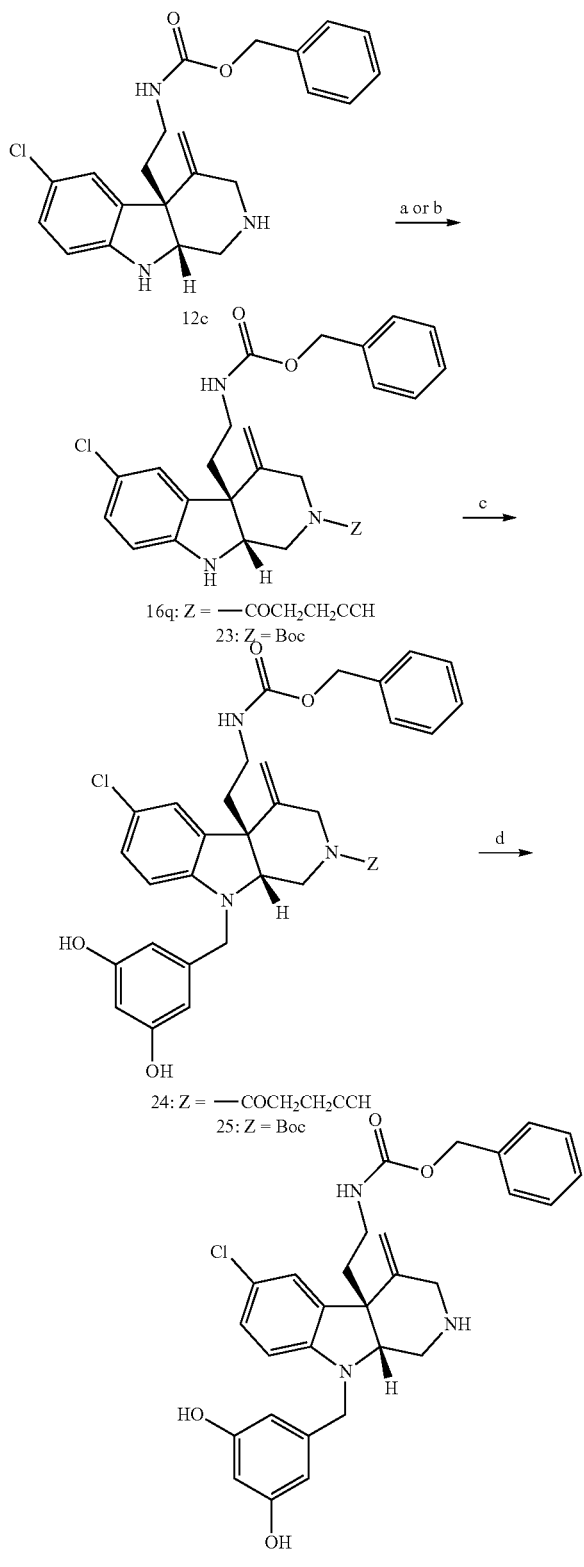

Reagents and conditions: a) Succimdyl ester, DCM, 0° C.; b) Boc₂O, DCM, 0° C.; c) 3,5-dihydroxybenzaldehyde, NaCNBH₃, AcOH, MeOH, 0° C.; d) TFA:DCM (1:1), 0° C.

The physiochemical properties of various compounds were evaluated. Compound ATI 13 was found to have a vastly improved physical properties. For example, the saturated concentration of ATI 13 was at 587 µg mL$^{-1}$, almost 300 fold its MRC in MRSA. In vivo pharmacokinetic (PK) properties of 13 was evaluated. A single dose (30 mg kg$^{-1}$) of 13, administered to mice through intraperitoneal (IP) injection was well tolerated with only minor clinical observations and 13 showed promising in vivo PK properties.

The half-life ($T_{1/2}$) of 13 was 2.5 hr and a maximum concentration ($C_{max}$) of 8.0 µg mL$^{-1}$ was reached quickly after 30 minutes. The area under the curve (AUC) to the last data point at 24 hr was 18.2 hr µg mL$^{-1}$, which matched the AUC calculated to infinity. Accordingly, it is expected that, similar to highly polar β-lactam antibiotics, 13 has low general membrane permeability. To test this, permeability assessments were performed using MDCK cells. The permeability of 13 was comparable to mannitol, which is a low permeability marker (i.e., 2.11E-06±3.53E-07 cm s$^{-1}$ for 13; 1.51E-06±2.67E-07 cm s$^{-1}$ for mannitol). For comparison, the permeability of metoprolol, a high permeability marker, was measured as 5.35E-05±6.05E-06 cm s$^{-1}$ in this assay. Despite low permeability in vitro, in vivo PK studies through IP delivery shows that 13 can reach plasma levels at approximately 4×MRC in MRSA. Overall, ATI 13 exhibited high aqueous solubility, low mammalian membrane permeability and good PK properties in vivo.

General Methods:

Unless otherwise noted, reagents were obtained commercially and used without further purification. Dichloromethane (DCM) was purchased from Fisher Chemical and distilled from CaH₂ under a nitrogen atmosphere prior to use. Toluene (Tol) was purchased from Sigma-Aldrich and distilled from CaH₂ under a nitrogen atmosphere prior to use. Triethylamine (TEA) and methanol (MeOH) were purchased from Fisher Chemical. Anhydrous carbon tetrachloride (CCl₄), acetonitrile (ACN), N,N-dimethylformamide (DMF) and 1,4-dioxane (Dioxane) were purchased from Sigma-Aldrich. Ethyl acetate (EtOAc) was purchased from Macron Fine Chemicals. Chloroform (CHCl₃) and hexanes (Hex) were purchased from EMD Chemicals. EtOAc, Hex, MeOH, CHCl₃ and TEA were used as elution solvents for thin-layer chromatography (TLC) and flash column chromatography.

Preparation of Cyclization Precursors (8a-j):

General Procedure A (Indole Synthesis Reaction): 4-Chloro-benzenesulfonyl chloride (6.33 g, 30 mmol) was added to a solution of 4-dimethylaminopyridine (DMAP) (3.67 g, 30 mmol) in anhydrous DMF (25 mL) at 0° C. The reaction was stirred at 23° C. for 30 minutes. A solution of 2-methyl-1-pyrroline (2.08 g, 25 mmol) in anhydrous DMF (25 mL) was added and the reaction was stirred at the same temperature for 1 hour. Methanesulfonic acid (4.87 mL, 75 mmol) was added to the reaction at 0° C. The reaction was then stirred at 23° C. for 2 hours. 4-Bromo-2-fluoro-phenyl hydrazine hydrochloride (9.06 g, 35.7 mmol) was added and stirred for an additional hour at 23° C. The reaction was then heated to 85° C. for 12 hours in a sealed tube. The reaction was then cooled to room temperature and concentrated in vacuo. The resulting residue was dissolved in ethyl acetate and washed with saturated aqueous solution of NaHCO₃ followed by brine. The combined organic layers were dried over anhydrous Na₂SO₄, filtered and concentrated in vacuo to give a crude product, which was purified by column chromatography on silica gel eluting with 70:30 Hex:EtOAc to give N-(2-(5-bromo-7-fluoro-2-methyl-1H-indol-3-yl)ethyl)-4-chlorobenzenesulfonamide (S1) as an off-white solid.

Using this procedure the following compounds were also prepared: N-(2-(5-bromo-2-methyl-1H-indol-3-yl)ethyl)-4-chlorobenzenesulfonamide (S2); Benzyl (2-(5-chloro-2-methyl-1H-indol-3-yl)ethyl)carbamate (S3); Benzyl (2-(5,7-dichloro-2-methyl-1H-indol-3-yl)ethyl)carbamate (S4; Benzyl (2-(5-fluoro-2-methyl-1H-indol-3-yl)ethyl)carbamate (S5).

General Procedure B (N,N'-diBoc Protection):

To a solution of S1 (2.75 g, 6.16 mmol, 12.3 mL, 0.50 M in DCM), DMAP (1.50 g, 12.3 mmol), TEA (1.71 mL, 12.3 mmol) and di-tert-butyl dicarbonate (Boc$_2$O) (3.36 g, 15.4 mmol) were added. The reaction was stirred at room temperature for 48 hours then washed with water and brine. The organic layer was then dried over Na$_2$SO$_4$ concentrated in vacuo to give a crude product, which was purified by column chromatography on silica gel eluting with 90:10 Hex:EtOAc to give tert-butyl 5-bromo-3-(2-((N-(tert-butoxycarbonyl)-4-chlorophenyl)sulfonamido)ethyl)-7-fluoro-2-methyl-1H-indole-1-carboxylate (7a) as a yellow.

Using this procedure the following compounds were also prepared: tert-butyl 5-bromo-3-(2-((N-(tert-butoxycarbonyl)-4-chlorophenyl)sulfonamido)ethyl)-2-methyl-1H-indole-1-carboxylate (7g);

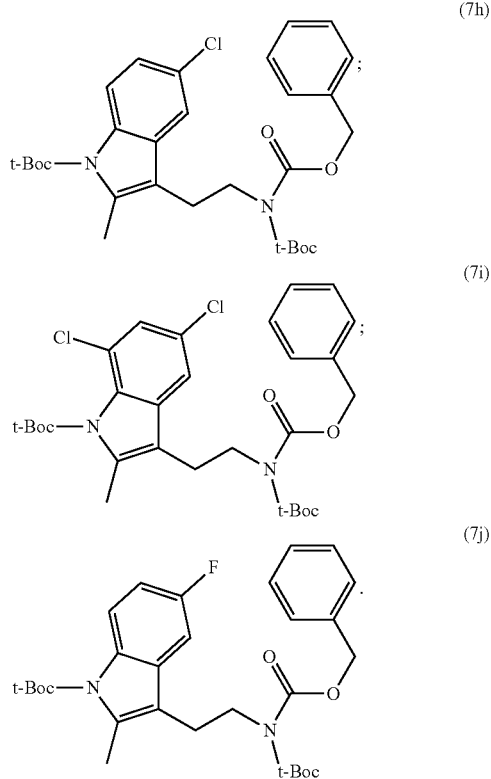

General Procedure C (Bromination of 7a):

N-Bromosuccinimide (NBS) (0.276 g, 1.54 mmol) and benzoyl peroxide (BPO) (0.050 g, 0.155 mmol) were added to a solution of 7a (1.00 g, 1.54 mmol, 6.2 mL, 0.25 M in CCl$_4$) followed by heating at 85° C. for 1 hour. Insoluble material was removed by filtering the crude reaction through celite, followed by concentration in vacuo to give tert-butyl 5-bromo-2-(bromomethyl)-3-(2-((N-(text-butoxycarbonyl)-4-chlorophenyl)sulfonamido)ethyl)-7-fluoro-1H-indole-1-carboxylate (10a), which was used directly in the next step without further purification.

General Procedure D (Alkylation of Propargyl Amine):

A solution of crude 10a (1.12 g, 1.54 mmol, 7.7 mL, 0.20 M in ACN) was added dropwise to a solution of propargyl amine (0.986 mL, 15.4 mmol, 10 M in ACN) at −10° C. over the course of 10 minutes. After addition of indole was complete, the reaction was stirred for 1 hour in the ice bath. The reaction was diluted 20× with EtOAc and washed with saturated bicarbonate solution followed by washing with brine. The organic layer was dried over anhydrous Na$_2$SO$_4$, filtered and concentrated in vacuo to give a crude product, which was purified by column chromatography on silica gel eluting with 50:48:2 Hex:EtOAc:TEA to give tert-butyl 5-bromo-3-(2-((N-(tert-butoxycarbonyl)-4-chlorophenyl)sulfonamido)ethyl)-7-fluoro-2-((prop-2-yn-1-ylamino)methyl)-1H-indole-1-carboxylate (S6) as a clear oil.

Similarly the corresponding compounds S7-S10 were prepared using General Procedures C and D from compounds 7(g)-7(j), respectively.

General Procedure E (Boc Deprotection):

Compound S6 (0.293 g, 0.419 mmol) was dissolved in 10 mL 1:1 TFA:DCM* then stirred at 0° C. for 2 hours. The solvent was then concentrated in vacuo to give a residue. The residue was diluted with EtOAc and washed with a saturated aqueous solution of NaHCO$_3$. The aqueous was then extracted 3× with EtOAc and the combined organic layers were washed with brine and dried over anhydrous Na$_2$SO$_4$, filtered and concentrated in vacuo to give N-(2-(5-bromo-7-fluoro-2-((prop-2-yn-1-ylamino)methyl)-1H-indol-3-yl)ethyl)-4-chlorobenzenesulfonamide (S11) which was used for the next step without further purification.

General Procedure F (Protection of Propargyl Amine):

To a solution of S11 (0.209 g, 0.419 mmol, 1.7 mL, 0.25 M in DCM) was added TEA (0.175 ml, 1.26 mmol), 4-nitro-benzensulfonyl chloride (NsCl) (0.098 g, 0.440 mmol) at 0° C. and warmed to room temperature. The reaction was stirred for 2 hours. The reaction was concentrated then diluted with EtOAc and washed with saturated aqueous solution of NaHCO$_3$. The organic layer was washed with water, brine and then separated and dried over anhydrous Na$_2$SO$_4$. Solids were removed via filtration and then solvent was removed in vacuo to give a crude product, which was purified by column chromatography on silica gel eluting with 70:30 Hex:EtOAc to give N-((5-bromo-3-(2-((4-chlorophenyl)sulfonamido)ethyl)-7-fluoro-1H-indol-2-yl)methyl)-4-nitro-N-(prop-2-yn-1-yl)benzenesulfonamide (8a) as a beige solid.

Alternative Procedure F' (Protection of Propargyl Amine):

TFAOSu (0.021 g, 0.100 mmol) was added to a solution of S11 (0.050 g, 0.100 mmol, 0.400 mL, 0.25 M in DCM) at 0° C. and warmed to room temperature. The reaction was stirred for 2 hours. The reaction was quenched by addition of a saturated aqueous solution of NaHCO$_3$ and then diluted with EtOAc. The organic layers were washed with water followed by brine. The organic layer was then dried over anhydrous Na$_2$SO$_4$. Solids were removed via filtration and then solvent was removed in vacuo to give a crude product, which was purified by column chromatography on silica gel eluting with 70:30 Hex:EtOAc to give N-((5-bromo-3-(2-((4-chlorophenyl)sulfonamido)ethyl)-7-fluoro-1H-indol-2-yl)methyl)-2,2,2-trifluoro-N-(prop-2-yn-1-yl)acetamide (8b) as a clear oil.

General Procedures E and F were employed using appropriate propargyl amine compounds and appropriate protecting groups to prepare the following compounds: N-(2-(5- bromo-7-fluoro-2-((N-(prop-2-yn-1-yl)methylsulfonamido) methyl)-1H-indol-3-yl)ethyl)-4-chlorobenzenesulfonamide (8c); N-((5-bromo-3-(2-((4-chlorophenyl)sulfon-amido)-ethyl)-7-fluoro-1H-indol-2-yl)methyl)-4-chloro-2-nitro-N-(prop-2-yn-1-yl)benzenesulfonamide (8d); N-((5-bromo-3-(2-((4-chlorophenyl)sulfonamido)ethyl)-7-fluoro-1H-indol-2-yl)methyl)-4-methyl-N-(prop-2-yn-1-yl) benzenesulfonamide (8e); Benzyl ((5-bromo-3-(2-((4-chlorophenyl)sulfonamido)ethyl)-7-fluoro-1H-indol-2-yl) methyl)(prop-2-yn-1-yl)carbamate (8f); N-((5-bromo-3-(2-((4-chlorophenyl)-sulfonamido)ethyl)-1H-indol-2-yl) methyl)-4-nitro-N-(prop-2-yn-1-yl)benzenesulfonamide (8g); Benzyl (2-(5-chloro-2-(((4-nitro-N-(prop-2-yn-1-yl) phenyl)sulfonamido)methyl)-1H-indol-3-yl)ethyl)carbamate (8h); Benzyl (2-(5,7-dichloro-2-(((4-nitro-N-(prop-2-yn-1-yl)phenyl)sulfonamido)methyl)-1H-indol-3-yl)ethyl) carbamate (8i); Benzyl (2-(5-fluoro-2-(((4-nitro-N-(prop-2-yn-1-yl)phenyl)sulfonamido)methyl)-1H-indol-3-yl)ethyl) carbamate (8j).

General Procedure G (Gold-Catalyzed Tandem Cyclization):

Compound 8a (40.0 mg, 0.058 mmol) was dissolved in anhydrous 1,4-dioxane (1.0 mL) in a sealed tube. 5 mol % of the catalyst XPhosAuNTf$_2$ (2.8 mg, 2.9 µmol) was added as a solid and the reaction was heated at 90° C. for 12 hours under argon atmosphere. The reaction mixture was then concentrated in vacuo with diatomaceous earth. The free flowing powder was used directly for column chromatography on silica gel eluting with 80:20 hexanes:ethyl acetate to afford tetracyclic indoline 9a (6-bromo-10((4-chlorophenyl)sulfonyl)-8-fluoro-4-methylene-2-((4-nitrophenyly)sulfonyl)-1,2,3,4-tetrahydro-9H-9a,4a-(epiminoethano)pyrido [3,4-b]indole) as a clear oil.

Similarly using General Procedure G with compounds 8b-8j the corresponding tetracyclic indoline compounds 9b-9j, respectively, were prepared.

General Procedure H (Reductive Ring-Opening Reaction):

A solution of TFA (1.0 mmol, 0.114 g, 0.077 mL) was prepared in THF (1.0 mL); 2 equivalents of TFA from this solution (0.117 mmol, 0.117 ml, 1.0 M in THF) were added to a solution of 9a (0.040 g, 0.058 mmol, 0.10 M) in a 10:1 mixture of THF:MeOH (0.580 mL) at 0° C. The reaction was warmed to ambient temperature and stirred for 1 hour. The reaction was concentrated from methanol three times then dissolved in ethyl acetate and the organic layer was washed with a saturated aqueous solution of NaHCO$_3$. The combined organic layers were dried over anhydrous Na$_2$SO$_4$, filtered and concentrated in vacuo to give a crude product, which was purified by column chromatography on silica gel with 60:40 hexanes:ethyl acetate to afford N-(2-((4aS,9aR)-6-bromo-8-fluoro-4-methylene-2-((4-nitrophenyl)sulfonyl)-1,2,3,4,9,9a-hexahydro-4aH-pyrido[3,4-b]indol-4a-yl)ethyl)-4-chlorobenzenesulfonamide (11a) as a yellow oil.

General Procedure H was used to prepare the following compounds from compounds 9b and 9c, respectively: N-(2-((4aS,9aR)-6-bromo-8-fluoro-4-methylene-2-(methylsulfonyl)-1,2,3,4,9,9a-hexahydro-4aH-pyrido[3,4-b]indol-4a-yl) ethyl)-4-chlorobenzenesulfonamide (11b); and N-(2-((4aS, 9aR)-6-bromo-8-fluoro-4-methylene-2-(2,2,2-trifluoroacetyl)-1,2,3,4,9,9a-hexahydro-4aH-pyrido[3,4-b] indol-4a-yl)ethyl)-4-chlorobenzenesulfonamide (11c).

Selective Deprotection:

Thiophenol (0.045 ml, 0.50 mmol) and K$_2$CO$_3$ (0.057 g, 0.50 mmol) were added to a solution of 11a (0.057 g, 0.083 mmol, 0.080 M) in anhydrous ACN. The reaction was refluxed under argon for 3 hours. The reaction was cooled to room temperature and the solvent was removed in vacuo to give a residue, which was dissolved in methanol then concentrated onto diatomaceous earth to give a free-flowing solid which was loaded onto an equilibrated silica gel chromatography column eluting with 90:8:2 DCM:MeOH: TEA to give N-(2-((4aS,9aR)-6-bromo-8-fluoro-4-methylene-1,2,3,4,9,9a-hexahydro-4aH-pyrido[3,4-b]indol-4a-yl) ethyl)-4-chlorobenzenesulfonamide (12) as a clear oil.

Preparation of Guanidine Derivatives:

A solution of compound 12 (0.011 g, 0.022 mmol, 0.070 M) was prepared in DCM (0.314 mL) and cooled to 0° C. To this solution, N,N-di-Boc-1H-pyrazole-1-carboxamidine (0.024 mmol, 7.5 mg) was added and the reaction was warmed to room temperature with stirring under argon for 12 hours. The crude reaction was diluted to 1 mL with DCM then washed with 2.0 N NaOH then brine. The organic layer was dried with Na$_2$SO$_4$ and concentrated in vacuo to give a clear residue which was purified by column chromatography eluting with 70:30 hexanes: ethyl acetate to give diBoc-Guanidine ATI which was used directly in the next step. DiBoc-Guanidine ATI was dissolved in 1 mL 1:1 DCM:TFA at 0° C. under argon and the reaction stirred for 4 hours. The reaction was then concentrated in vacuo to give a trifluoroacetic acid salt of (4aS,9aR)-6-bromo-4a-(2-((4-chlorophenyl)sulfonamido)ethyl)-8-fluoro-4-methylene-1,3,4,4a,9, 9a-hexahydro-2H-pyrido[3,4-b]indole-2-carboximidamide (13) as a white solid.

Preparation of trifluoroacetic acid salt of 2-((4aS,9aR)-6-bromo-4a-(2-((4-chlorophenyl)sulfonamido)ethyl)-8-fluoro-4-methylene-1,3,4,4a,9,9a-hexahydro-2H-pyrido[3, 4-b]indol-2-yl)acetic acid (14). A solution of compound 12 (0.024 g, 0.048 mmol, 0.070 M) was prepared in DCM (0.686 mL) and cooled to 0° C. under argon. A solution of tert-butylbromoacetate (1.0 mmol, 0.195 g, 0.148 mL) in DCM (1 mL) was prepared. One equivalent (0.048 ml, 0.048 mmol, 1.0 M in DCM) of this solution and TEA (0.020 mL, 0.144 mmol) were then added to the solution of 12 dropwise at 0° C. The reaction was then stirred for 3 hours at room temperature. The organic layer was diluted with DCM and washed with 2.0 N NaOH followed by brine. The organic layer was dried over Na$_2$SO$_4$ and then concentrated in vacuo to give a residue which was purified by column chromatography eluting with 50:48:2 Hex:EtOAc:TEA to give a tert-butyl ester of compound 14, which was used in the next step directly. Tert-butyl ester of compound 14 was dissolved in 1.0 mL DCM:TFA 1:1 and cooled to 0° C. followed by stirring under argon for 2 hours. The reaction was then concentrated in vacuo to give a yellow residue of trifluoroacetic acid salt of compound 14 as a yellow oil (38% yield for 2 steps, 0.012 g, 0.018 mmol).

Examples 2: Polycyclic Indolenine Compounds

Bridged polycyclic indolenines are a prevalent structural motif in natural indole alkaloids. Many of these share a common tetracyclic core and have anti-inflammatory and anti-infective activity. However, the bridged indolenine framework (e.g., such as those present in scholarisine H, akuammiline, 10,11-dimethoxynareline, strictamine, picrinine and quebrachidine) has been proven difficult to construct. This example provides a facile synthesis of bridged tetracyclic indolenines using a gold-catalyzed desilylative cyclization reaction. Antimicrobial screens of the cyclized products also showed that compounds of the invention also selectively repress β-lactam resistance in MRSA.

The silylated cyclization precursor 10a (Scheme 2-1) was prepared from indole 7 by sequential treatment with NaH and tert-butyldimethylsilyl (TBS) chloride.

Scheme 2-1

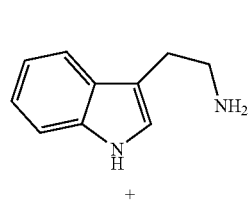

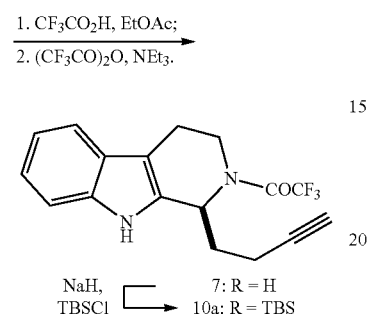

With the substrate 10a in hand, a various catalysts and reaction conditions were used for cyclization (Table 2-1). As can be seen, IPrAuBF4-catalyzed desilylative cyclization of 10a using MeOH as the silyl scavenger and proton source gave a good yield of the desired product.

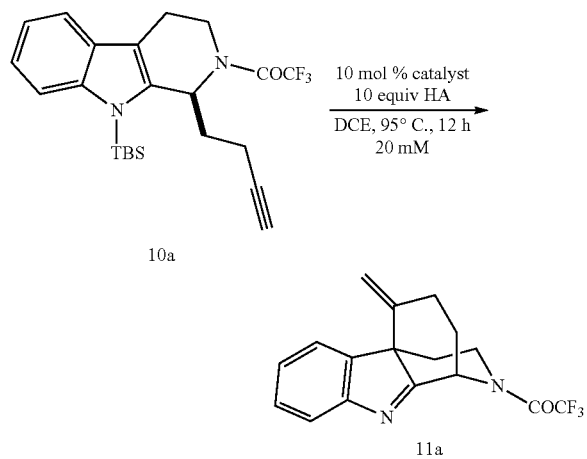

TABLE 2-1

Reaction Conditions

| Entry | Catalyst | HA | Consumption [%][a] | Yield [%][a] |
|---|---|---|---|---|
| 1 | AuCl₃ | MeOH | 51 | 6 |
| 2 | Ph₃PAuNTf₂ | MeOH | 100 | 0 |
| 3 | PtCl₂ | MeOH | 37 | 0 |
| 4 | IMesAuBF₄ | MeOH | 52 | 27 |
| 5 | IPrAuBF₄ | MeOH | 82 | 67(66)[b] |
| 6 | IPrAuOTf | MeOH | 100 | 0 |
| 7 | IPrAuSbF₆ | MeOH | 43 | 7 |
| 8 | IPrAuBF₄ | i-PrOH | 64 | 20 |
| 9 | IPrAuBF₄ | H₂O | 63 | 27 |
| 10 | IPrAuBF₄ | pNO₂PhOH | 60 | 22 |

[a]1 equivalent of 4-(dimethylamino)pyridine was added as internal standard before taking ¹H NMR. Consumptions of 10a and yields were calculated based on ¹H NMR integration.
[b]Number in parenthesis is isolated yield (80% brsm).

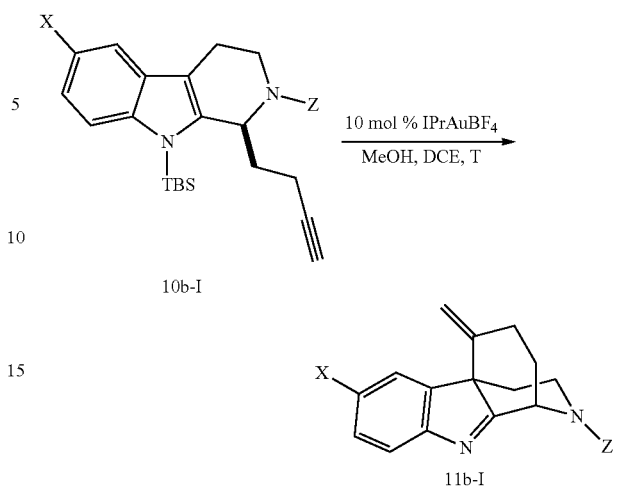

TABLE 2-2

| Entry | 10 | X | Z | MeOH (eq.) | T (° C.) | Yield [%] |
|---|---|---|---|---|---|---|
| 1 | 10b | H | COPh$^p$Cl | 20 | 90 | 66 |
| 2 | 10c | H | Ns | 20 | 70 | 86 |
| 3 | 10d | H | SO₂Ph$^p$Cl | 10 | 55 | 64 |
| 4[a] | 10e | H | Ts | 15 | 85 | 65 |
| 5 | 10f | H | Cbz | 20 | 100 | 53[b] |
| 6[c] | 10g | MeO | COCF₃ | 20 | 95 | 66 |
| 7[a] | 10h | MeO | Ns | 5 | 55 | 78 |
| 8[d] | 10i | Cl | COCF₃ | 20 | 105 | 44 |
| 9[e] | 10j | Cl | Ns | 5 | 70 | 66 |
| 10[e] | 10k | Cl | SO₂Ph$^p$F | 15 | 105 | 51 |
| 11 | 10l | H | COCF3 | | 95 | |

[a]50 mM.
[b]78% yield brsm.
[c]15 mol % IPrAuBF4, 100 mM.
[d]20 mol % IPrAuBF4, 100 mM.
[e]15 mol % IPrAuBF4, 50 mM.

Table 2-2 shows representative tetracyclic indolenine compounds that were prepared using this reaction. Substrates bearing a variety of functional groups on the tryptamine nitrogen (e.g., amide, carbamate, and sulfonamides) and/or on the 5-position of indole (e.g., MeO, H, and Cl) were prepared in the racemic forms. All substrates were converted to the tetracyclic indolenines. A variety of functional groups were suitable at the amine nitrogen.

Tetracyclic indolenine compounds were then evaluated in a series of bacterial whole-cell assays. Compound 11b potentiated the activity of methicillin in a multi-drug resistant MRSA strain, ATCC BAA-44. To assess the degree of synergy between 11b and methicillin, a checkerboard minimum inhibitory concentration (MIC) study was performed. The Fractional Inhibitory Concentration Index (FICI) of these two compounds was determined to be 0.039 (≤0.5) in BAA-44, indicating that a strong synergistic effect.

TABLE 2-3

Potentiation Profile of 11b in MRSA BAA-44.

| Antibiotic | MIC (µg/mL) | MIC (+11b)[a] (µg/mL) | Fold of potentiation |
|---|---|---|---|
| Methicillin | 128 | 8 | 16 |
| Oxacillin | 32 | 1 | 32 |

TABLE 2-3-continued

Potentiation Profile of 11b in MRSA BAA-44.

| Antibiotic | MIC (µg/mL) | MIC (+11b)[a] (µg/mL) | Fold of potentiation |
|---|---|---|---|
| Amox/clav | 16 | 2 | 8 |
| Cefazolin | 128 | 4 | 32 |
| Meropenem | 4 | 1 | 4 |

[a]MIC value was determined in the presence of 10 µM 11b.

The MICs of a variety of antibiotics in the presence and absence of 11b, respectively. In addition to methicillin, BAA-44 is also resistant to a wide range of antibiotics, such as tetracycline, erythromycin, and daptomycin. As shown in Table 2-3, compound 11b potentiates the activity of all β-lactams tested, such as oxacillin, amox/clav, cefazolin, and meropenem. Without being bound by any theory, it is believed compound 11b and other compounds of the invention are selective potentiators of β-lactams.

The minimum re-sensitizing concentrations (MRCS) of 11b to re-sensitize a variety of MRSA strains to β-lactam antibiotics, amox/clav and cefazolin was also evaluated. In addition to BAA-44, other CA-MRSA strains (NRS-100 (a.k.a., COL) and NRS-384 (a representative strain of the highly prevalent CA-MRSA type USA 300) were also evaluated as well as VRSA strains, NR-46414 and NR-46421. The MRCS of 11b were found in the range of 0.25-2 µg/mL in all strains tested. Furthermore, 11b showed low antibacterial activity on its own with MICs of 32-64 µg/mL in all strains tested, and low mammalian toxicity with a half growth inhibitory concentration (GI50) of 41 µg/mL in human cervical carcinoma (HeLa) cells.

Compound 11l was used to prepare a variety of analogues. The trifluoroacetamide of 11l was removed under basic conditions to give a secondary amine 12. This intermediate was functionalized further with alkyl halides, acyl chlorides, sulfonyl chlorides, or EDC mediated coupling with carboxylic acids (Scheme 2-2).

Scheme 2-2.

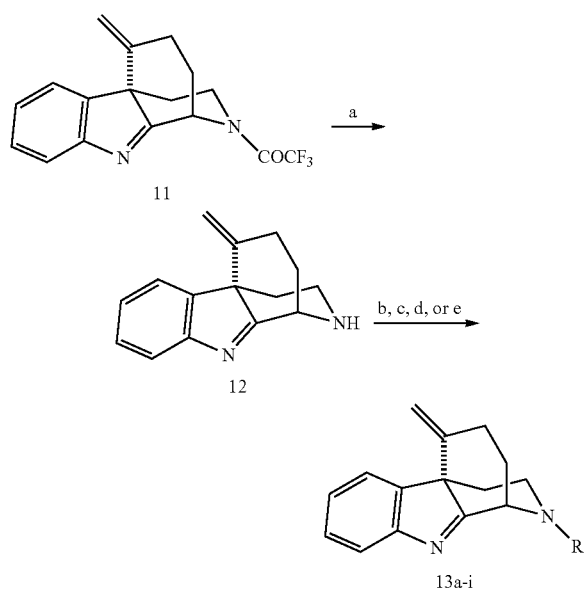

13a (R = —COCH$_2$(tetrahydro-2H-pyran-4-yl)); 13b (R = —COCH$_2$NH-tBoc);
13c (R = —CO(1-methylpiperidin-4-yl)); 13d (R = —COCH$_2$(morpholino));
13e (R = —CO(pyridin-3-yl)); 13f (R = —CO(6-chloropyridin-3-yl)); 13g (R = —COCH$_2$(4-methylpiperazin-1-yl)); 13h (R = —CO(2-methyloxazol-4-yl));
13i (R = (1-methyl-1H-imidazol-4-yl)sulfonyl)

Reagents and Conditions: a) K$_2$CO$_3$, THF:H$_2$O (10:1); b) Acyl Chloride, TEA, DCM; c) RCOOH, 1-Ethyl-3-(3-dimethylaminopropyl)carbodiimide, TEA, DCM; d) RSO$_2$Cl, TEA, DCM; e) RCH$_2$Br, TEA, DCM.

General procedure A (Pictet-Spengler reaction):

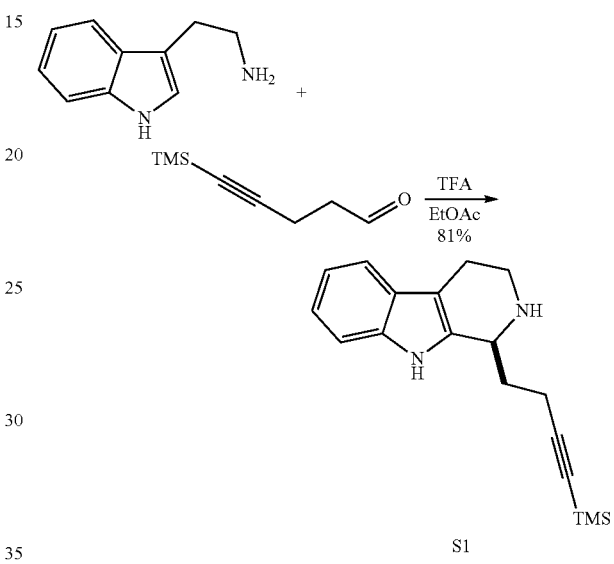

To tryptamine (2.00 g, 12.5 mmol) in dry EtOAc (25.0 mL) at 0° C. was added aldehyde (0.960 g, 6.24 mmol) followed by slow addition of TFA (1.49 mL, 25.0 mmol). Another portion of aldehyde (2.89 g, 18.7 mmol) was added within 3 h through syringe pump. The resulting mixture was stirred at 25° C. for 12 h before cooled to 0° C. The solution was basified with 2 M NaOH (13.0 mL). The aqueous layer was extracted with DCM (50 mL×3). The combined organic phases were dried over Na$_2$SO$_4$, filtered and concentrated. Purification by flash chromatography (20:1 DCM/MeOH) provided the pure product (3.00 g, 81%) as a yellowish oil.

Using this procedure, the following compounds were also prepared: 6-Methoxy-1-[4-(trimethylsilyl)but-3-yn-1-yl]-1H,2H,3H,4H,9H-pyrido[3,4-b]indole (S4); 6-Chloro-1-(4-(trimethylsilyl)but-3-ynyl)-2,3,4,9-tetrahydro-1H-pyrido[3,4-b]indole (S7).

General Procedure B (Desilylative Reaction):

To substrate S1 (3.00 g, 10.1 mmol) in THF (33.0 mL) at 0° C. was added 1 M TBAF (12.0 mL, 12.0 mmol). The reaction solution was warmed to 25° C. and stirred at 25° C. for 1 h before quenched with water (15 mL). The aqueous layer was extracted EtOAc (40 mL×3), dried over Na$_2$SO$_4$, decanted and concentrated. Purification by flash chromatography (20:1 DCM/MeOH) provided the pure product S2 (desilylated S1) (2.27 g, 100%) as a yellow solid.

Using this procedure, the following compounds were also prepared: 1-(But-3-yn-1-yl)-6-chloro-1H,2H,3H,4H,9H-pyrido[3,4-b]indole (S8).

General Procedure C (Protection of Secondary Amine):

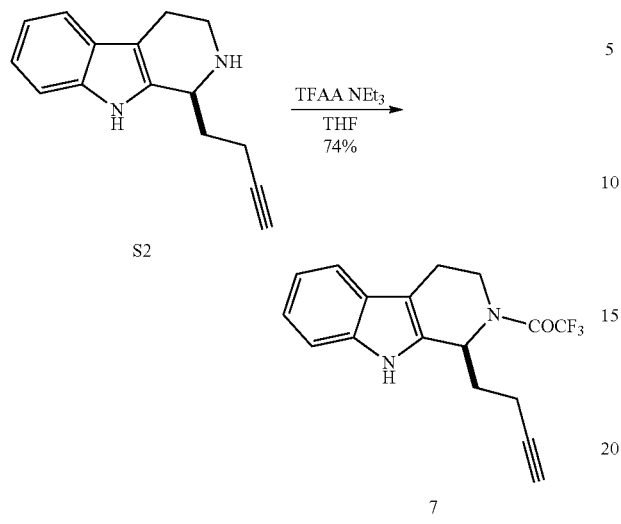

General Procedure D (N$^{in}$-Silyl Group Installation):

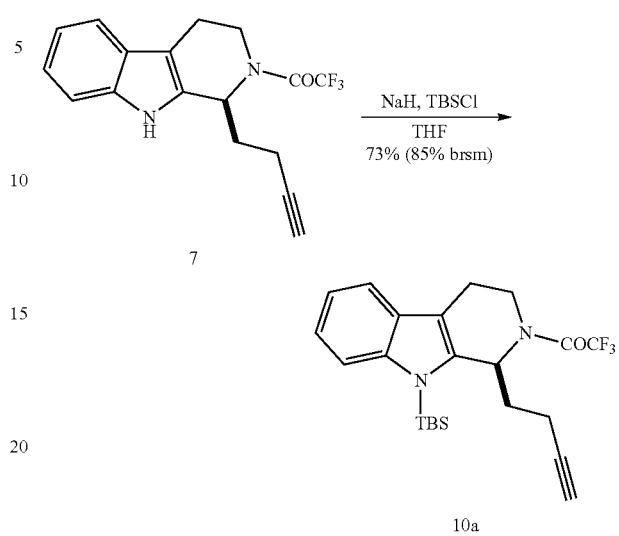

Compound S2 (0.138 g, 0.460 mmol) was dissolved in THF (4.50 mL) and the resulting reaction solution was cooled to −78° C. Et$_3$N (0.390 mL, 2.77 mmol) and TFAA (0.190 mL, 1.38 mmol) were added. After stirring at −78° C. for 2 h, the reaction solution was diluted with EtOAc (50 mL), warmed to 25° C., then washed with saturated NH$_4$Cl (5 mL) and brine (5 mL), dried over Na$_2$SO$_4$, filtered and concentrated. Purification by flash chromatography (10:1 Hexanes/EtOAc) provided the pure product 7 (0.110 g, 74%) as a white solid.

Using this procedure the following compounds were also prepared: 1-(But-3-yn-1-yl)-9-(tert-butyldimethylsilyl)-2-(4-chlorobenzoyl)-1H,2H,3H,4H,9H-pyrido[3,4-b]indole (10b); 1-(But-3-ynyl)-9-(tert-butyldimethylsilyl)-2-(4-nitrophenylsulfonyl)-2,3,4,9-tetrahydro-1H-pyrido[3,4-b]indole (10c); 1-(But-3-yn-1-yl)-9-(tert-butyldimethylsilyl)-2-(4-chlorobenzenesulfonyl)-1H,2H,3H,4H,9H-pyrido[3,4-b]indole (10 d); 1-(But-3-yn-1-yl)-9-(tert-butyldimethylsilyl)-2-[(4-methylbenzene)sulfonyl]-1H,2H,3H, 4H,9H-pyrido[3,4-b]indole (10e); Benzyl 1-(but-3-yn-1-yl)-9-(tert-butyldimethylsilyl)-1H,2H,3H,4H,9H-pyrido[3,4-b]indole-2-carboxylate (10f); 1-(But-3-yn-1-yl)-6-methoxy-1H,2H,3H,4H,9H-pyrido[3,4-b]indole (S5); 1-[1-(But-3-yn-1-yl)-9-(tert-butyldimethylsilyl)-6-methoxy-1H,2H,3H,4H,9H-pyrido[3,4-b]indol-2-yl]-2,2,2-trifluoroethan-1-one (10g); 1-(But-3-yn-1-yl)-9-(tert-butyldimethylsilyl)-6-methoxy-2-[(4-nitrobenzene)sulfonyl]-1H,2H,3H,4H,9H-pyrido[3,4-b]indole (10h); 1-[1-(But-3-yn-1-yl)-9-(tert-butyldimethylsilyl)-6-chloro-1H,2H,3H,4H,9H-pyrido[3,4-b]indol-2-yl]-2,2,2-trifluoroethan-1-one (10i); 1-(But-3-yn-1-yl)-9-(tert-butyldimethylsilyl)-6-chloro-2-[(4-nitrobenzene)sulfonyl]-1H,2H,3H,4H,9H-pyrido[3,4-b]indole (10j); 1-(But-3-yn-1-yl)-9-(tert-butyldimethylsilyl)-6-chloro-2-[(4-fluorobenzene)sulfonyl]-1H,2H,3H,4H,9H-pyrido[3,4-b]indole (10k).

To NaH (2.32 g, 58.1 mmol, 60% in mineral oil) in THF (240 mL) at 0° C. was slowly added the solution of substrate (15.5 g, 48.4 mmol) in THF (60.0 mL). The reaction mixture was stirred at 25° C. for 30 min before cooled to 0° C. The solution of TBSCl (8.75 g, 58.1 mmol) in THF (60.0 mL) was slowly added. The mixture was warmed to 25° C. and stirred for 12 h before quenched with water (50 mL). The aqueous layer was extracted with EtOAc (150 mL×3), washed with brine (50 mL), dried over Na$_2$SO$_4$, filtered and concentrated. Purification by flash chromatography (50:1, then 10:1 Hexanes/EtOAc) provided the silylated product (15.3 g, 73% yield and 85% based on recovery of starting material) as a white solid and unreacted starting material (2.16 g, 14%) as a yellowish solid.

Using this procedure the following compounds were also prepared: 1-(1-(But-3-ynyl)-9-(triethylsilyl)-3,4-dihydro-1H-pyrido[3,4-b]indol-2(9H)-yl)-2,2,2-trifluoroethanone (10-TES); 1-(But-3-ynyl)-9-(tert-butyldimethylsilyl)-2,3,4,9-tetrahydro-1H-pyrido[3,4-b]indole (S3); 1-(But-3-yn-1-yl)-9-(tert-butyldimethylsilyl)-6-methoxy-1H,2H3H,4H,9H-pyrido[3,4-b]indole (S6); 1-(But-3-yn-1-yl)-9-(tert-butyldimethylsilyl)-6-chloro-1H,2H,3H,4H,9H-pyrido[3,4-b]indole (S9).

General Procedure E:

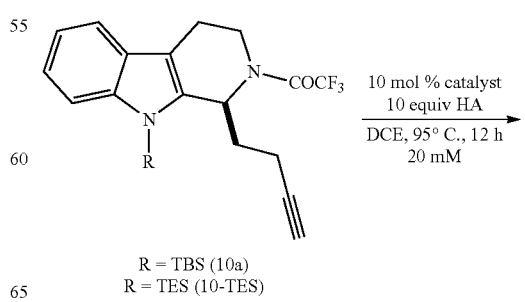

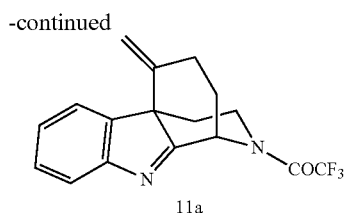

11a

To a 20 mL sealed tube containing IPrAuCl (4 mg, 6.9 µmol) and DCE (0.15 mL) was added the solution of AgBF$_4$ (1 mg, 6.9 µmol) in toluene (0.3 mL). The resulting mixture was stirred for 5 min. To prepared solution of catalyst was added the solution of alkynyl indole 10a (30 mg, 69 µmol) in DCE (3 mL) followed by methanol (28 µL, 0.69 mmol). The reaction solution was stirred at 95° C. for 12 h before cooled to 25° C. The solution was filtered through a short plug of silica gel and concentrated. Purification by flash chromatography (50:1, then 7:1 Hexanes/EtOAc) provided unconsumed starting material 10a (5.4 mg, 18%) as a white solid and the pure product 11a (14.5 mg, 66%) as a white solid.

Using this procedure the following compounds were also prepared: 11-[(4-Chlorophenyl)carbonyl]-14-methylidene-8,11-diazatetracyclo[8.3.3.0$^{1,9}$.0$^{2,7}$]hexadeca-2(7),3,5,8-tetraene (11b); 14-Methylidene-11-[(4-nitrobenzene)sulfonyl]-8,11-diazatetracyclo[8.3.3.0$^{1,9}$.0$^{2,7}$]hexadeca-2(7),3,5,8-tetraene (11c); 11-[(4-Chlorobenzene)-sulfonyl]-14-methylidene-8,11-diazatetracyclo[8.3.3.0$^{1,9}$.0$^{2,7}$]hexadeca-2(7),3,5,8-tetraene (11d); 11-[(4-Methylbenzene)sulfonyl]-14-methylidene-8,11-diazatetracyclo[8.3.3.0$^{1,9}$.0$^{2,7}$]-hexadeca-2(7),3,5,8-tetraene (11e); Benzyl 14-methylidene-8,11-diazatetracyclo-[8.3.3.0$^{1,9}$.0$^{2,7}$]hexadeca-2(7),3,5,8-tetraene-11-carboxylate (11f); 2,2,2-Trifluoro-1-{4-methoxy-14-methylidene-8,11-diazatetracyclo[8.3.3.0$^{1,9}$.0$^{2,7}$]hexadeca-2(7),3,5,8-tetraen-11-yl}ethan-1-one (11g); 4-Methoxy-14-methylidene-11-[(4-nitrobenzene)sulfonyl]-8,11-diazatetracyclo[8.3.3.0$^{1,9}$.0$^{2,7}$]hexadeca-2(7),3,5,8-tetraene (11h); 1-{4-Chloro-14-methylidene-8,11-diazatetracyclo[8.3.3.0$^{1,9}$.0$^{2,7}$]hexadeca-2(7),3,5,8-tetraene (11)-yl}-2,2,2-trifluoroethan-1-one (11i); 4-Chloro-14-methylidene-11-[(4-nitrobenzene)sulfonyl]-8,11-diazatetracyclo[8.3.3.0$^{1,9}$.0$^{2,7}$]hexadeca-2(7),3,5,8-tetraene (11j); 4-Chloro-11-[(4-fluorobenzene)sulfonyl]-14-methylidene-8,11-diazatetracyclo[8.3.3.0$^{1,9}$.0$^{2,7}$]hexadeca-2(7),3,5,8-tetraene (11k).

Synthesis of 14-Methylidene-8,11-diazatetracyclo [8.3.3.0$^{1,9}$.0$^{2,7}$]hexadeca-2,4,6,8-tetraene (S10)

To compound 11a (40 mg, 0.13 mmol) in MeOH/H$_2$O (1.2 mL, 1:1) was added K$_2$CO$_3$ (80 mg, 0.58 mmol). After stirring at 25° C. for 12 h, the solvent was evaporated and water was added. The aqueous layer was extracted with chloroform (10 ml×3) and the combined organic phases were dried over Na$_2$SO$_4$, decanted and concentrated. Purification by flash chromatography (12:1 DCM/MeOH) provided the deprotected product (27 mg, 96%) as a yellowish oil.

Biological Assay:

Strain ATCC BAA-44 was gift from the laboratory of Daniel Feldheim. Strains NRS100, NRS384, NR-46414, and NR-46421 were obtained from BEI Resources (beiresources.org). HeLa cells were purchased from ATCC (atcc.org).

The minimal inhibitory concentrations (MICS) of antimicrobial compounds and 11b were determined by the broth microdilution method detailed in the Clinical and Laboratory Standards Institute (CLSI) handbook. All antimicrobial compounds were purchased from Sigma-Aldrich. The growth media used for all MIC experiments was Mueller Hinton Broth (MHB) purchased from HIMEDIA through VWR (cat: 95039-356). The inoculum was prepared by diluting a bacterial day culture (OD$_{600}$ 0.15-0.4) to OD$_{600}$ 0.002. This dilution was further diluted two fold when added to 96 well microplates (USA Scientific CytoOne 96-well TC plate, cat: CC7682-7596) for a final inoculum concentration of OD$_{600}$ 0.001. All plates were incubated at 37° C. with shaking for 18 hours before results were interpreted.

The MRSA strain ATCC BAA-44 was used to determine the MIC values of various antimicrobial compounds in the presence of 10 µM 11b. The experiment was conducted similarly to the CLSI MIC determination described previously; however, MHB was supplemented with 20 µM 11b prior to set up and inoculation. The final concentration of 11b after inoculation with BAA-44 was 10 µM.

Antibiotic MIC values where S. aureus is considered susceptible were determined from the CLSI handbook. MHB was supplemented with the antimicrobial at a concentration two fold greater than the CLSI susceptible MIC value. Two-fold serial dilutions of 11b were prepared in antibiotic supplemented media in 96-well microplates. These were inoculated with MRSA diluted to OD$_{600}$ 0.002 and incubated at 37° C. with shaking for 18 hours before results were interpreted. The concentration of 11b in antibiotic supplemented media at which there was no observable growth was considered the minimum resensitizing concentration (MRC). For amoxicillin/clavulanic acid, the initial concentration was 8/4 µg/mL; for cefazolin, 16 µg/mL. A 50 µL portion of the antibiotic containing media was added to each well of 96-well plates, and 100 µL was added to the top row. A 1.28 µL portion of 5 mg/mL 11b was added to the top row of each plate to afford a concentration of 64 µg/mL in the top row of each plate, and 2-fold serial dilutions were performed down the columns. Once the plates were prepared, a day culture of MRSA was diluted to OD$_{600}$ 0.002, and 50 µL was added to each well. The final concentration of MRSA added was OD$_{600}$ 0.001, the final concentration of amoxicillin/clavulanic acid was 4/2 µg/mL, the final concentration of cefazolin was 8 µg/mL, and the highest concentration of 11b tested was 32 µg/mL. Plates were incubated overnight at 37° C. with shaking. The MRC value was determined as the concentration of 11b in the presence of antibiotic at which there was no observable overnight growth.

To evaluate the cytotoxicity of 11b in mammalian cells, a cell viability assay was carried out using CellTiter-Glo luminescent cell viability assay kit (Promega). Human cervical adenocarcinoma HeLa cells were seeded on white, cell-culture treated 96-well plates (Corning: 3917) with Dulbecco's modified Eagle's medium (DMEM) supplemented with 10% fetal calf serum (FCS), 1% penicillin/streptomycin, at the densities of 20,000 cells/well. The medium volume for each well was 100 µL. Cells were incubated at 37° C. in 5% CO$_2$/95% air for 16 hours. The medium was removed from each well and replaced with 99 µL of warmed fresh medium. To each well was then added 1.0 µL of 11b in DMSO with the final concentrations of 1.56-200 µg/mL. Each concentrate was performed in two replicates. After incubation at 37° C. for another 24 hours, the plates were equilibrated to room temperature for 30 minutes. 100 µL of CellTiter-Glo reagent (Promega) was added to each well and mixed for 2 minutes on an orbital shaker. The plate was incubated at room temperature for another 10 minutes to stabilize luminescent signal. The luminescence of each sample was recorded in an Envision Multilabel Plate Reader (Perkin Elmer).

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. All references cited herein are incorporated by reference in their entirety.

What is claimed is:

1. A compound of the formula:

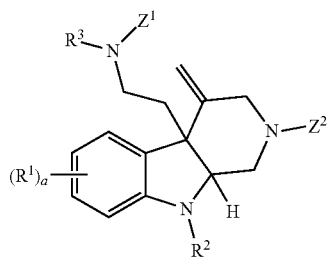

A wherein
a is 0, 1 or 2;
each $R^1$ is independently halide;
each of $R^2$, $R^3$ and $Z^1$ is independently hydrogen, alkyl or a nitrogen protecting group, provided at most only one of $Z^1$ or $R^3$ is a nitrogen protecting group; and
$Z^2$ is hydrogen, alkyl, a nitrogen protecting group, heteroalkyl or a carbonyl group.

2. The compound according to claim 1, wherein a is 1 or 2.

3. The compound according to claim 1, wherein each of $R^1$ is independently selected from the group consisting of hydrogen, Cl, Br, and F.

4. The compound according to claim 1 of the formula:

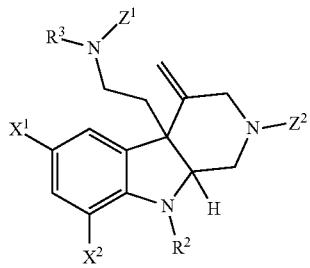

wherein $R^2$, $R^3$, $Z^1$ and $Z^2$ are those defined in claim 1; and each of $X^1$ and $X^2$ is independently selected from the group consisting of hydrogen, Cl, Br and F, provided at least one of $X^1$ and $X^2$ is not hydrogen.

5. The compound according to claim 4, wherein $X^2$ is F.

6. The compound according to claim 4, wherein $X^1$ is Cl.

7. The compound according to claim 1, wherein $Z^2$ is selected from a moiety of the group consisting of: —C(=O)$R^a$, —C(=O)[CH$_2$]$_2$CCH, —C(=O)CH$_2$NH-tBoc, —C(=O)CH$_2$NH$_2$, —C(=O)[CH$_2$]$_5$NHC(=O)[CH$_2$]$_2$—$Y_1$, —C(=O)[CH$_2$]$_3$Y$^2$, —C(=O)[CH$_2$]$_2$CO$_2$H, —C(=O)CF$_3$, —C(=O)Y$^3$, -tBoc, —SO$_2$—Ar$^1$, —C(=O)NHY$^4$, and a guanidine derivative of the formula —C(=NR$^x$)—NR$^y$R$^z$ where each of R$^x$, R$^y$ and R$^z$ is independently selected from the group consisting of H, alkyl, cycloalkyl, heterocycloalkyl, (heterocycloalkyl)alkyl, (cycloalkyl)alkyl, and heteroalkyl; R$^a$ is alkyl or haloalkyl, Ar$^1$ is aryl or heteroaryl, $Y^1$ is 5,5-difluoro-7,9-dimethyl-5H-4λ$^4$,5λ$^4$-dipyrrolo[1,2-c:2',1'-f][1,3,2]diazaborinin-3-yl, $Y^2$ is (3aS,4S,6aR)-2-oxohexahydro-1H-thieno[3,4-d]imidazol-4-yl, $Y^3$ is cycloalkyl, (heterocycloalkyl)alkyl, heterocycloalkyl, aryl, heteroaryl and $Y^4$ is alkyl, heterocycloalkyl or (heterocycloalkyl)alkyl.

8. The compound according to claim 7, wherein $R^a$ is methyl, ethyl, heptyl, trifluoromethyl.

9. The compound according to claim 7, wherein Ar$^1$ is selected from the group consisting of 4-chlorophenyl, 1-methyl-1H-imidazol-4-yl and 6-chloropyridin-3-yl.

10. The compound according to claim 7, wherein $Y^3$ is selected from the group consisting of 4,4-difluorocyclohexyl, 4-chlorophenyl, (tetrahydro-2H-pyran-4-yl)methyl, 1-(2,2,2-trifluoroacetyl)piperidin-4-yl, 1-(2,2,2-trifluoroacetyl)azetidin-3-yl, 6-chloropyridin-3-yl and (morpholino)methyl.

11. The compound according to claim 7, wherein $Y^4$ is selected from the group consisting of methyl, tetrahydro-2H-pyran-4-yl and tetrahydrofuran-2-yl)methyl.

12. An antibiotic composition comprising a compound of claim 1.

13. The antibiotic composition of claim 12 further comprising a β-lactam antibiotic.

14. The antibiotic composition of claim 13 further comprising a β-lactamase inhibitor or other resistance-modifying agent or a combination thereof.

15. A method for treating bacterial infection in a subject comprising administering to the subject in need of such a treatment a therapeutically effective amount of a compound of claim 1.

16. A method for treating methicillin-resistant *Staphylococci aureus* infection in a subject comprising administering to the subject having a MRSA infection a therapeutically effective amount of a composition comprising a compound of claim 1 and a β-lactamase inhibitor.

17. The method of claim 16, wherein the β-lactamase inhibitor comprises amoxicillin, clavulanic acid, cefazolin, meropenem, or a combination thereof.

* * * * *